United States Patent [19]

Purchio et al.

[11] Patent Number: 5,221,620

[45] Date of Patent: Jun. 22, 1993

[54] CLONING AND EXPRESSION OF TRANSFORMING GROWTH FACTOR β2

[75] Inventors: Anthony F. Purchio; Linda Madisen, both of Seattle, Wash.; Nancy Webb, College Station, Tex.

[73] Assignee: Oncogen, Seattle, Wash.

[21] Appl. No.: 446,020

[22] Filed: Dec. 5, 1989

Related U.S. Application Data

[63] Continuation-in-part of Ser. No. 285,140, Dec. 16, 1988, abandoned, which is a continuation-in-part of Ser. No. 234,065, Aug. 18, 1988, abandoned, which is a continuation-in-part of Ser. No. 148,267, Jan. 25, 1988, abandoned, which is a continuation-in-part of Ser. No. 106,752, Oct. 6, 1987, abandoned.

[51] Int. Cl.$^5$ .................. C12P 21/02; C12P 19/34; C12N 15/00; C12N 7/00; C12N 5/00; C07K 3/00

[52] U.S. Cl. .................. 435/69.7; 455/69.1; 455/69.5; 455/91; 455/172.3; 455/235.1; 455/240.2; 530/350; 935/19; 935/32; 935/34; 935/47; 935/57; 935/62; 935/70

[58] Field of Search .............. 435/69.1, 91, 172.3, 435/235, 320.1, 240.2; 530/350; 526/37; 935/18, 32, 34, 57, 61, 70, 19, 62

[56] References Cited

U.S. PATENT DOCUMENTS

| | | | |
|---|---|---|---|
| 4,338,397 | 7/1982 | Gilbert et al. | 435/68 |
| 4,399,216 | 8/1983 | Axel et al. | 435/6 |
| 4,546,082 | 10/1985 | Kujan et al. | 437/172.3 |
| 4,708,948 | 11/1987 | Iwata et al. | 514/2 |
| 4,774,322 | 9/1988 | Seyedin et al. | 530/353 |

FOREIGN PATENT DOCUMENTS

| | | |
|---|---|---|
| 105014 | 4/1984 | European Pat. Off. . |
| 128849 | 12/1984 | European Pat. Off. . |
| 155433 | 9/1985 | European Pat. Off. . |
| 200341 | 12/1986 | European Pat. Off. . |
| 268561 | 5/1988 | European Pat. Off. . |
| 293785 | 12/1988 | European Pat. Off. . |
| WO85/04421 | 10/1985 | PCT Int'l Appl. . |

OTHER PUBLICATIONS

Kaijhn et al. Invest. Urol. vol. 17 pp. 16-23 (1979).
Sharples et al. DNA vol. 6 pp. 239-244 (1987).
Ikeda et al Biochemistry vol. 26 pp. 2406-2410 (1987).
Suges et al Proc Natl Acad Sci USA vol. 78 pp. 6613-6617 (1981).
Kaufman et al. Mol. Cell. Biol. vol. 5 pp. 1750-1759 (1985).
Estin et al. Proc. Natl. Acad. Sci USA vol. 85 pp. 1052-1056 (1988).
Richard Palmiter et al. Growth of Mice Bearing mThGH Fusion Genes vol. 222 pp. 809-814.
Dunn et al. J. Mol. Biol. (1983) pp. 477-535.
Subramani et al. Analysis of Gene Expression using Simian Virus 40 Vectors pp. 1-15 vol. 135 (1983).
Mansour et al Proc. Natl. Acad. Sci. USA pp. 1359-1363 vol. 82 (1985).
Haj-Ahmad et al. J. of Virol. pp. 267-274 vol. 57 (1986).
Cochran et al Proc. Natl. Acad. Sci USA vol. 82 pp. 19-23 (1985).
Taub et al. pp. 222-230 (1982).
Young et al. Efficient isolation of genes by using antibody probes pp. 1194-1198 vol. 80 (1983).
Yanisch-Perron et al Gene vol. 33 pp. 103-119 (1985).
Valenzuela et al. Nature vol. 298 pp. 347-350 (1982).
Kramer et al. HTLV-III. vol. 231 pp. 1580-1584 (1986).

(List continued on next page.)

Primary Examiner—Joan Ellis
Attorney, Agent, or Firm—Pennie & Edmonds

[57] ABSTRACT cDNA clones coding for TGF-β2 which are used to construct expression vectors capable of directing the high-level expression of mature, biologically active TGF-β2, as well as precursor TGF-β2 forms, in transfected Chinese Hamster Ovary cells (CHO cells) and transfected COS cells are described. CHO and COS transfectants secreting TGF-β2 at high levels are also described. CHO cells transfected with a plasmid vector carrying the complete 414 amino acid simian TGF-β2 precursor secrete approximately 5 µg per ml culture media.

2 Claims, 29 Drawing Sheets

OTHER PUBLICATIONS

Maeda et al. Prod. of HumaαInterferon in Silkworm using a baculo virus vector vol. 315 pp. 592–595.
Kuroda et al. EMBO Journal vol. 5 pp. 1359–1365 (1986).
Kaufman et al. J. Mol. Biol. vol. 159 pp. 601–621 (1982).
Itakura et al Science vol. 209 pp. 1401–1405 (1980).
Talmadge et al Gene vol. 12 pp. 235–241 (1980).
Brunner et al., 1988, Mol. Cell. Biol. 8 (No. 5): 2229–2232.
Cate et al., 1986, Cell 45: 685–698.
Centrella et al., 1987, J. Biol. Chem. 262 (No. 6): 2869–2874.
Cheifetz et al., 1987, Cell 48: 409–415.
Coffey et al., 1988, Cancer Res. 48: 1596–1602.
Derynck et al., 1985, Nature 316: 701–705 ("Derynck I").
Derynck et al., 1986, J. Biol. Chem. 261 (No. 10): 4377–4379 ("Derynck II").
Derynck et al., 1987, Nucleic Acids Res. 15 (No. 7): 3188–3189 ("Derynck III").
Derynck et al., 1988, EMBO J. 7 (No. 12): 3737–3743 ("Derynck IV").
Gentry et al., 1987, Mol. Cell. Biol. (No. 10): 3418–3427 ("Gentry I").
Gentry et al., 1988, Mol. Cell. Biol. 8 (No. 10): 4162–4168 ("Gentry II").
Goey et al., 1989, J. Immunol. 143 (No. 3): 877–880.
Ignotz et al., 1986, J. Biol. Chem. 261 (No. 9): 4337–4345.
Ikeda et al., 1987, Biochemistry 26: 2406–2410.
Jakowlew et al., 1988, Mol. Endocrinol. 2 (No. 8): 747–755 ("Jakowlew I").
Jakowlew et al., 1988, Mol. Endocrinol. 2 (No. 12): 1186–1195 ("Jakowlew II").
Kasid et al., 1988, J. Immunol. 141 (No. 2): 690–698.
Kehrl et al., 1986 J. Exp. Med. 163: 1037–1050 ("Kehrl I").
Kehrl et al., 1986, J. Immunol. 137 (No. 12): 3855–3860 ("Kehrl II").
Kovacina et al., 1989, Biochem. Biophys. Res. Commun. 160 (No. 1): 393–403.
Marquardt et al., 1987, J. Biol. Chem. 262 (No. 25): 12127–12131.
Mason et al., 1985, Nature 318: 659–663.
McPherson et al., 1989, Biochemistry 28: 3442–3447.
Mustoe et al., 1987, Science 237: 1333–1336.
Noda et al., 1989, Endocrinology 124 (No. 6): 2991–2994.
Padgett et al., 1987, Nature 325: 81–84.
Purchio et al., 1988, J. Biol. Chem. 263 (No. 28): 14211–14215.
Ranchalis et al., 1987, Biochem. Biophys. Res. Commun. 148 (No. 2): 783–789.
Reiss et al., 1988, In Vitro Cell. Dev. Biol. 24 (No. 6): 537–544.
Roberts et al., 1981, Proc. Natl. Acad. Sci. USA 78 (No. 9): 5339–5343 ("Roberts I").
Roberts et al., 1985, Proc. Natl. Acad. Sci. USA 82: 119–123 ("Roberts II").
Seyedin et al., 1987, J. Biol. Chem. 262 (No. 5): 1946–1949.
Sharples et al., 1987, DNA 6 (No. 3): 239–244.
Sporn et al., 1986, Science 233: 532–534.
Ten Dijke et al., 1988, Proc. Natl. Acad. Sci. USA 85: 4715–4719.
Wahl et al., 1988, J. Immunol. 140 (No. 9): 3026∝3032.
Wakefield et al., 1989, Growth Factors 1: 203–218.
Wrann et al., 1987, EMBO J. 6 (No. 6): 1633–1636.

```
-467    GCCCCTCCCGTCAGTTGCGGCCAGCTGCCAGCCCCGGGACCTTTCATCTCTTCCCTTGGCCGGAGGAGCC                    -397
        GAGTTCAGATCCGCCACTCCGCACCCGAGACTGACACACTCCACTTCCTCCTCTAAATTTATTTCTACTTAATAGCCACTGTCTCTTTTT  -298
        CCCATCTCATTGCTCCAAGAATTTTTTTCTTACTCGCCAAAGTCAGGGTTCCCTCTGCCCGTCCCGTATTAATATTTCCACTTTTGAACTACTG  -199
        GCCTTTTCTTTTAAAGGAATTCAAGCAGGATACGTTTTCTGTGGGCATTGACTGTTGCAAAAGTTTCGCATCAAAAACAACAACAAA       -100
        AAACCAAACAACTCTCCTGATCTATACTTTGAGAATTGTGATTTCTTTTTTATTCTGACTTTTAAAAAACAACTTTTTTTTCCACTTTTTAAAAA  -1

MET His Tyr Cys Val Leu Ser Ala Phe Leu Ile Leu His Leu Val Thr Val Ala Leu Ser Leu Ser Thr Cys Ser    75
ATG CAC TAC TGT GTG CTG AGC GCT TTT CTG ATC CTG CAT CTG GTC ACG GTC GCG CTC AGC CTG TCT ACC TGC AGC
                                                             20

Thr Leu Asp Met Asp Gln Phe Met Arg Lys Arg Ile Glu Ala Ile Arg Gly Gln Ile Leu Ser Lys Leu Lys Leu   150
ACA CTC GAT ATG GAC CAG TTC ATG CGC AAG AGG ATC GAG GCG ATC CGC GGG CAG ATC CTG AGC AAG CTG AAG CTC
                 T                           35

Thr Ser Pro Pro Glu Asp Tyr Pro Glu Pro Glu Glu Val Pro Pro Glu Val Ile Ser Ile Tyr Asn Ser Thr Arg   225
ACC AGT CCA CCA GAA GAC TAT CCT GAG CCC GAG GAA GTC CCC CCG GAG GTG ATT TCC ATC TAC AAC AGC ACC AGG
                               60                                                *

Asp Leu Leu Gln Glu Lys Ala Ser Arg Arg Ala Ala Ala Cys Glu Arg Arg Ser Arg Glu Glu Asp Glu Tyr Tyr Ala   300
GAC CTC CAG GAG AAG GCG AGC CGG AGG GCG GCC GCC TGC GAG CGC AGG AGC AGG GAG GAG GAC GAA TAC TAC GCC
                              85

Lys Glu Val Tyr Lys Ile Asp Met Pro Pro Phe Phe Pro Ser Glu Thr Val Cys Pro Val Val Thr Thr Pro Ser   375
AAG GAG GTT TAC AAA ATA GAC ATG CCG CCC TTC TTC CCC TCC GAA ACT GTC TGC CCA GTT GTT ACA ACA CCC TCT
                             110                       120

Gly Ser Val Gly Ser Leu Cys Ser Arg Gln Val Leu Cys Gly Tyr Leu Asp Ala Ile Pro Pro Thr Phe   450
GGC TCA GTG GGC AGC TTG TGC TCC AGA CAG TCC CAG GTG CTC TGT GGG TAC CTT GAT GCC ATC CCG CCC ACT TTC
                   135                                                  145

FIG. 1A
```

```
Tyr Arg Pro Tyr Phe Arg Ile Val Arg Asp Val Ser Ala Met Glu Lys Asn Ala Ser Asn Leu Val Lys Ala
TAC AGA CCC TAC TTC AGA ATT GTT CGA TTT GAC GTC TCA GCA ATG GAG AAG AAT GCT TCC AAT TTG GTG AAA GCA       525
                                160                             *  170                    195
                                 G

Glu Phe Arg Val Phe Arg Leu Gln Asn Pro Lys Ala Arg Val Pro Glu Gln Arg Ile Glu Leu Tyr Gln Ile Leu
GAG TTC AGA GTC TTT CGT TTG CAG AAC CCA AAA GCC AGA GTG CCT GAA CAA CGG ATT GAG CTA TAT CAG ATT CTC       600
            185                             210                              220            G

Lys Ser Lys Asp Leu Thr Ser Pro Thr Gln Arg Tyr Ile Asp Ser Lys Val Val Lys Thr Arg Ala Glu Gly Glu
AAG TCC AAA GAT TTA ACA TCT CCA ACC CAG CGC TAC ATC GAC AGC AAA GTT GTG AAA ACA AGA GCA GAA GGC GAA       675
        C                                       235                        245

Trp Leu Ser Phe Asp Val Thr Asp Ala Val His Glu Trp Leu His His Lys Asp Arg Asn Leu Gly Phe Lys Ile
TGG CTC TCC TTC GAT GTA ACT GAT GCT GTT CAT GAA TGG CTT CAC CAT AAA GAC AGG AAC CTG GGA TTT AAA ATA       750
    T                                                       260                       *  270

Ser Leu His Cys Pro Cys Cys Thr Phe Val Pro Ser Asn Asn Tyr Ile Ile Pro Asn Lys Ser Glu Glu Leu Glu
AGC TTA CAC TGT CCC TGC TGC ACT TTT GTA CCA TCT AAT AAT TAC ATC ATC CCA AAT AAA AGT GAA GAA CTA GAA       825
                                                    285                            T 295

Ala Arg Phe Ala Gly Ile Asp Gly Thr Ser Thr Tyr Thr Ser Gly Asp Gln Lys Thr Ile Lys Ser Thr Arg Lys
GCA AGA TTT GCA GGT ATT GAT GGC ACC TCC ACA TAT ACC AGT GGT GAT CAG AAA ACT ATA AAG TCC ACT AGG AAA       900
                                                                310                        320

Lys Asn Ser Gly Lys Thr Pro His Leu Leu Leu Met Leu Pro Ser Tyr Arg Leu Gly Ser Gln Gln Thr Asn
AAA AAC AGT GGG AAG ACC CCA CAT CTC CTG CTA ATG TTA CCC TAC AGA CTT GAG TCA CAA CAG ACC AAC              975
                                                                            335

Arg Arg Lys Lys Arg Ala Leu Asp Ala Ala Tyr Cys Phe Arg Asn Val Gln Asp Asn Cys Cys Leu Arg Pro Leu
CGG AGA AAG AAG CGT GCT TTG GAT GCG GCC TAT TGC TTT AGA AAT GTG CAG GAT AAT TGC TGC CTA CGT CCA CTT    1050
                                                345                                            G
```

FIG. 1B

```
                                      360
Tyr Ile Asp Phe Lys Arg Asp Leu Gly Trp Lys Trp Ile His Glu Pro Lys Gly Tyr Asn Ala Asn Phe Cys Ala
TAC ATT GAT TTC AAG AGG GAT CTA GGG TGG AAA TGG ATA CAC GAA CCC AAA GGG TAC AAT GCC AAC TTC TGT GCT    1125
                                385                                   370
Gly Ala Cys Pro Tyr Leu Trp Ser Ser Asp Thr Gln His Ser Arg Val Leu Ser Leu Tyr Asn Thr Ile Asn Pro
GGA GCA TGC CCG TAT TTA TGG AGT TCA GAC ACT CAG CAC AGC AGG GTC CTG AGC TTA TAT AAT ACC ATA AAT CCA    1200
                                      395
                                      410
Glu Ala Ser Ala Ser Pro Cys Cys Val Ser Gln Asp Leu Pro Leu Thr Ile Leu Tyr Tyr Ile Gly Lys Thr
GAA GCA TCT GCT TCT CCT TGC TGC GTG TCC CAA GAT TTA GAA CCT CTA ACC ATT CTC TAC TAC ATT GGC AAA ACA    1275
                        C                           420
                                      435          442  ***
Pro Lys Ile Glu Gln Leu Ser Asn Met Ile Val Lys Ser Cys Lys Cys Ser
CCC AAG ATT GAA CAG CTT TCT AAT ATG ATT GTA AAG AGT TGC AAA TGC AGC  TAA  AATTCTTGGAAAGTGGCAAGACCAAA   1356

ATGACAATGATGATGATGATGACGACGACAACGATGATGCTTGTAACAAGAAAACATAAGAGAGCCTTGGTTCATCAGTGTTAAAAATTTT           1456
GAAAGGCGGGTACTAGTTCAGACACTTTGGAAGTTTGTGTTCTCGTTTGTTAAAAACTGGCCATCTGACACTCTGACACACAAAAAGTTGAAGGCCTTATTCTACATTTC   1556
ACCTACTTTGTAAGTGAGAGAGACAAGAACAAAATAACACTGGAAGAATTTATTAGTGTTAATTATGTGAACAACGACA                      1656
ACAACAACAACAACAACAGGAAATCCCATTAAGTGGAGTTGCTGTGTACCGTTCCTATCCCGCCCTCACTTGATTTTTCTGTATTGCTATG         1756
CAATAGGCACCCCTTCCCATTCTTACTCTCTTAGAGTTAACACAGTGAGTTATTGTGTGTTACTATATAATGAACGTTTCATTGCCCTTGAAAATAAAA   1856
CAGGTGTATAAGTGAGACCAAATACTTTGCCAGAAACTCATGGATGGCTTAAGAACTGAACTCAAACGAGCCAGAAAAAAGAGGTCATATTAAT       1956
GGGATGAAACCCAAGTGAGTTATTATATGACCGAGAAGTCTGCATTAAGATAAAGACCCTGAAAACACATGTTATGTATCAGTCGTGCCTAAGGAAGCT   2056
TCTTGTAAGGTCCAAAAACTAAAAGAACTGTTAATAAAGAAACTTTCAGTCAG(poly A)                                        2111
```

FIG. 1C

```
-261  AGGGATCTGTGGCAGGTCGGAGA---AAGATC---CGTCTCCTGTGTACCAGATCTCGCCCATCTAGGTT              -198

ATTTCCGGTGGATACTGAGACACCCCGGTCCAAGCCTCCCACCACTGCGCCCTTCCTCGAGGA-CCTCAACTTTCCCTCGAGGCCCTCCTAC   -100

CTTTTCCCGGGGACCCCCAGCCCCTGCAGGGGGGGGCCTCCCACCAAACTAGCCTCTCGGCAGTGCCGGGGGGCGCCGCCTCCCCC          -1

Met Pro Pro Ser Gly Leu Arg Leu Leu Leu Pro Leu Leu Leu Trp Leu Leu Val Leu Thr Pro Ser Arg    75
      ATG CCG CCC TCC GGG CTG CGG CTG CTG CTG CCG CTG CTA CTG TGG CTA CTG GTG CTG ACG CCT AGC CGG
                              10                            20

Pro Ala Ala Gly Leu Ser Thr Cys Lys Thr Ile Asp Met Glu Leu Val Lys Arg Lys Arg Ile Glu Thr Ile Arg  150
      CCG GCC GCA GGA CTA TCC ACC TGC AAG ACT ATC GAC ATG GAG CTG GTG AAG CGG AAG CGC ATC GAG ACC ATC CGC
                              35                            45

Gly Gln Ile Leu Ser Lys Leu Arg Leu Ala Ser Pro Pro Ser Gln Gly Glu Val Pro Pro Gly Pro Leu Pro Glu  225
      GGC CAG ATC CTG TCC AAG CTG CGC CTC GCC TCC CCC AGC CAG GGG GAG GTG CCC CCC GGC CCG CTG CCC GAG
                              60                            70

Ala Val Leu Ala Leu Tyr Asn Ser Thr Arg Asp Arg Val Ala Gly Glu Ser Ala Glu Pro Glu Pro Glu  300
      GCC GTG CTC GCC CTG TAC AAC AGC ACC CGC GAC CGG GTG GCC GGG GAG AGT GCG GAG CCC GAA CCG GAG
                              85                            95

Ala Asp Tyr Tyr Ala Lys Glu Val Thr Arg Val Leu Met Val Glu Thr His Asn Glu Ile Tyr Asp Lys Phe Lys  375
      GCC GAC TAC TAC GCC AAG GAG GTC ACC CGC GTG CTA ATG GTG GAA ACC CAC AAC GAA ATC TAT GAC AAG TTC AAG
                              110                           120

Gln Ser Thr His Ser Ile Tyr Met Phe Phe Asn Thr Ser Glu Leu Arg Glu Ala Val Pro Glu Pro Val Leu Leu  450
      CAG AGC ACA CAC AGC ATA TAT ATG TTC TTC AAC ACA TCA GAG CTC CGA GAA GCA GTA CCT GAA CCT GTG TTG CTC
                              135                           145

Ser Arg Ala Glu Leu Arg Leu Leu       Arg Leu Lys Leu Lys Val Glu Gln His Val Glu Leu Tyr Gln Lys Tyr  522
      TCC CGG GCA GAG CTG CGT CTG CTG   ——   AGG CTC AAG CTC AAA GTG GAG CAG CAT GTG GAG CTG TAC CAG AAA TAC
                              160                           170
```

```
                                              185
Ser Asn Asn Ser Trp Arg Tyr Leu Ser Asn Arg Leu Leu Ala Pro Ser Asn Ser Pro Glu Trp Leu Ser Phe Asp
AGC AAC AAT TCC TGG CGA TAC CTC AGC AAC CGG CTG CTG GCG CCC AGC AAC TCG CCG GAG TGG TTG TCT TTT GAT    597
                                                          195
                                                                                                      672
Val Thr Gly Val Val Arg Gln Trp Leu Ser Arg Gly Gly Ile Glu Gly Phe Arg Gly Phe Arg Leu Ser Ala His Cys Ser
GTC ACC GGT GTC GTG CGG CAG TGG TTG AGC CGG GGA GGG GAA ATT GAG GGC TTT CGC AGC CTT AGC GCC CAC TGC TCC
                                                          210                                        
                                                                                                      747
Cys Asp Ser Lys Asp Asn Thr Leu Gln Val Asp Ile Asn Gly Phe Thr Thr Gly Arg Arg Gly Asp Leu Ala Thr
TGT GAC AGC AAG GAT AAC ACA CTG CAA GTG GAC ATC AAC GGG TTC ACT ACC GGC CGA GGT GAC CTG GCC ACA
                                235                                       245
                                                                                                      822
Ile His Gly Met Asn Arg Pro Phe Leu Leu Met Ala Thr Pro Leu Glu Arg Ala Gln His Leu Gln Ser Ser
ATT CAT GGC ATG AAC CGG CCT TTC CTG CTC ATG GCC ACC CCA CTG GAG AGG GCC CAA CAT CTG CAA AGC TCC
                        260                                       270
                                                                                                      894
Arg His Arg Arg Ala Leu Asp Ala Ala Tyr Cys Phe Arg Asn Val Gln Asp Asn Cys Cys Leu Arg Pro Leu
CGG CAC CGC CGA |GCT TTG GAT GCT GCC TAT TGC TTT AGA AAT GTG CAG GAT AAT TGC TGC CTA CGT CCA CTT|
                                285                                       295         G
                                                                                                      969
Tyr Ile Asp Phe Lys Arg Asp Leu Gly Trp Lys Trp Ile His Glu Pro Lys Gly Tyr Asn Ala Asn Phe Cys Ala
TAC ATT GAT TTC AAG AGG GAT CTA GGG GAT TGG AAA TGG ATA CAC GAA CCC AAA GGG TAC AAT GCC AAC TTC TGT GCT
                                310                                       320         A
                                                                                                      1044
Gly Ala Cys Pro Tyr Leu Trp Ser Ser Asp Thr Gln His Ser Arg Val Leu Ser Leu Tyr Asn Thr Ile Asn Pro
GGA GCA TGC CCG TAT TTA TGG AGT TCA GAC ACT CAG CAC AGC AGG GTC CTG AGC TTA TAT AAT ACC ATA AAT CCA
                        335                                       345
                                                                                                      1119
Glu Ala Ser Pro Cys Cys Val Ser Gln Asp Leu Glu Pro Leu Thr Ile Leu Tyr Tyr Ile Gly Lys Thr
GAA GCA TCT CCT TGC TGC GTG TCC CAA GAT TTA GAA CCT CTA ACC ATT CTC TAC ATT GGC AAA ACA
                360                                       370               C
```

```
                    385                390
pro Lys Ile Glu Gln Leu Ser Asn Met Ile Val Lys Ser Cys Lys Cys Ser   390
CCC AAG ATT GAA CAG CTT TCT AAT ATG ATT GTA AAG TCT TGC AAA TGC AGC ***  TAA AATTCTTGAAAAGTGGCAAGACCAAA   1200

ATGACAATGATGATGATAATGATGACGACGACAACGATGATGCTTGTAACAAGAAAACATAAGAGAGCCTTGGTTCATCAGTGTTAAAAAATTTTT   1299

GAAAAGGGCGGTACTAGTTCAGACACTTTGGAAGTTTGTGTTCTGTTTGTTAAAACTGGCATCTGACACAAAAAAAGTTGAAGGCCTTATTCTACATTTC   1398

ACCTACTTTGTAAGTGAGAGAGACAAGAAGCAAATTTTTTTAAAGAAAAAAATAAACACTGAAGAATTTATTAGTGTTAATTATGTGAACAACGACA   1497

ACAACAACAACAACAACAGGAAAATCCCATTCTTACTCTTAGAGTTAACAGTGAGTTATTATTGTGTACTATATAATGAACGTTTCATTGCCCTTGTACCGTATG   1596

CAATAGGCACCCTTCCCATTCTTACTCTTAGAGTTAACAGTGAGTTATTATTGTGTACTATATAATGAACGTTTCATTGCCCTTGAAAATAAAA   1695

CAGGTGTATAAAGTGGAGACCAAATACTTTGCCAGAACTCATGGATGGCTTAAGGAACTTGAACTCAAACGAGCCAGAAAAAAGAGGTCATATTAAT   1794

GGGATGAAACCCAAGTGAGTTATTATATGACCGAGAAAGTCTGCATTAAGATAAAGACCCTGAAAACAGATGTTATGTATCAGCTGCCTAAGGAAGCT   1893

TCTTGTAAGGTCCAAAAACTAAATAAAAGACTGTTAATAAAAGAAACTTTCAGTCAG(poly A)   1947
```

FIG. 1F

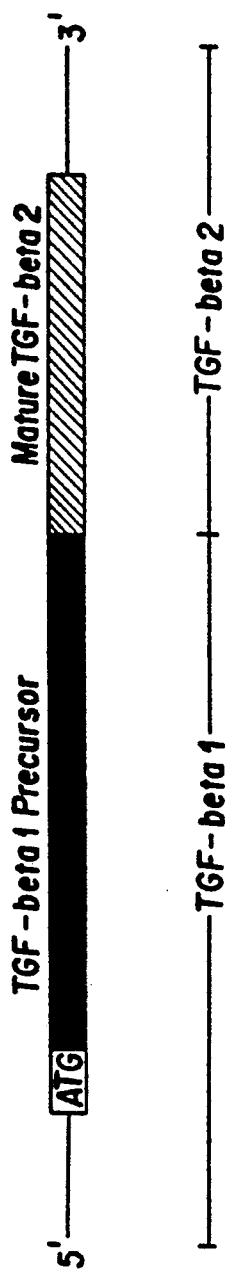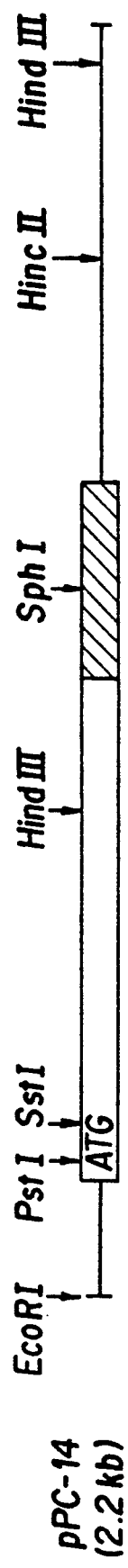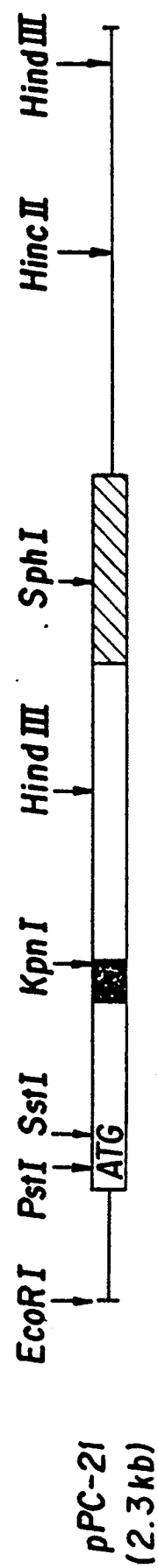
FIG. 1G
FIG. 1H

```
101                                                             115
Lys Glu Val Tyr Lys Ile Asp Met Pro Pro Phe Phe Pro Ser Glu Asn Ala Ile Pro Pro Thr Phe Tyr Arg Pro Tyr Phe Arg Ile Val   130
AAG GAG GTT TAC AAA ATA GAC ATG CCG CCC TTC TTC CCC TCC GAA AAT GCC ATC CCG ACT TTC TAC AGA CCC TAC TTC AGA ATT GTT
                                                                                                               pPC-14
                                                                                                              (2.2kb)

Thr Val Cys Pro Val Val Thr Thr Pro Ser Gly Ser Val Gly Ser leu Cys Ser Arg Gln Ser Gln Val Leu Cys Gly Tyr Leu Asp
ACT GTC TGC CCA GTT GTC ACA ACA CCC TCT GGC TCA GTG GGC AGC TTG TGC TCC AGA CAG TCC CAG GTG CTC TGT GGG TAC CTT GAT
                                                                                                        KpnI   pPC-21
                                                                                                              (2.3kb)
```

FIG. 1I

```
Beta 1    1  MPPSCLRLLPLLWLLVLTPGPPAAG LSTCKTIDMELVKRKRI
Beta 2    1  -MHYCVLSA-FLILHLVT----- -VALSTCSTLDMDQFMRKRI Beta 1   47  FAIRGQILSKLRLASPPSQGEVPPGPLPEAVLALYNSTRDRVAGES
Beta 2   38  EAIRGQILSKLKLTSPP-EEDYPEPPEVISIYNSTRDLLQEKA Beta 1   93  --AEPEPEADYYAKEVTRVLMVETHNEIYDKFKQSTHS---
Beta 2   83  SRRAACERERSDEEYYAKEVYKIDHPPFFPSETVCPVTTPSGSV Beta 1  131  --------IYMFFNTSELREAVPEPVL--LSR
Beta 2  129  CSLCSRQSVLCGYLDAIPPTFYRPYFRIVRFDVSAMEKNASNLVK Beta 1  153  AELRLLRRL--KLKV-EQHVELVQ---KYSNNSWRYLSNRLLAP
Beta 2  175  AEFRVFRLQNPKARVPEQRIELYQILKSKDLTSPTQRYIDSKVVKT Beta 1  191  SDSPEWLSFDVTGCVRQWLSRGGEIEGFRLSAHCSCDS------
Beta 2  221  RAEGEHLSFDVTDAVHEWLHKDRNLGFKISLHCPCCTFVPSNNYI Beta 1  229  --RDNTLQVDING-----FTTGRRGDLATIHGMN--RPFLLM
Beta 2  267  IPNKSEELEARFAGIDGTSTYTSGDQKTIKSTRKKNSGKTPHLLM Beta 1  263  ATPLERAQQHLQSSRHRRALDTNYCFSSTEKNCCVRQLYIDFRKDL
Beta 2  313  LLPSYRLESQQTNKRKRALDAAYCFRNVQDNCCLRPLYIDFKRDL Beta 1  309  GWKWIHEPKGYHANFCLGPCPYIWSLDTQYSKVLALYNQHNPGASA
Beta 2  359  GWKWIHEPKGYNANFCAGACPYLWSSDTQHSRVLSLYNTINPEASA Beta 1  355  APCCVPQALEPLPIVYYVGRKPKVEQLSNMIVRSCKCS
Beta 2  405  SPCCVSQDLEPLTILYYIGKTPKIEQLSNMIVKSCKCS
```

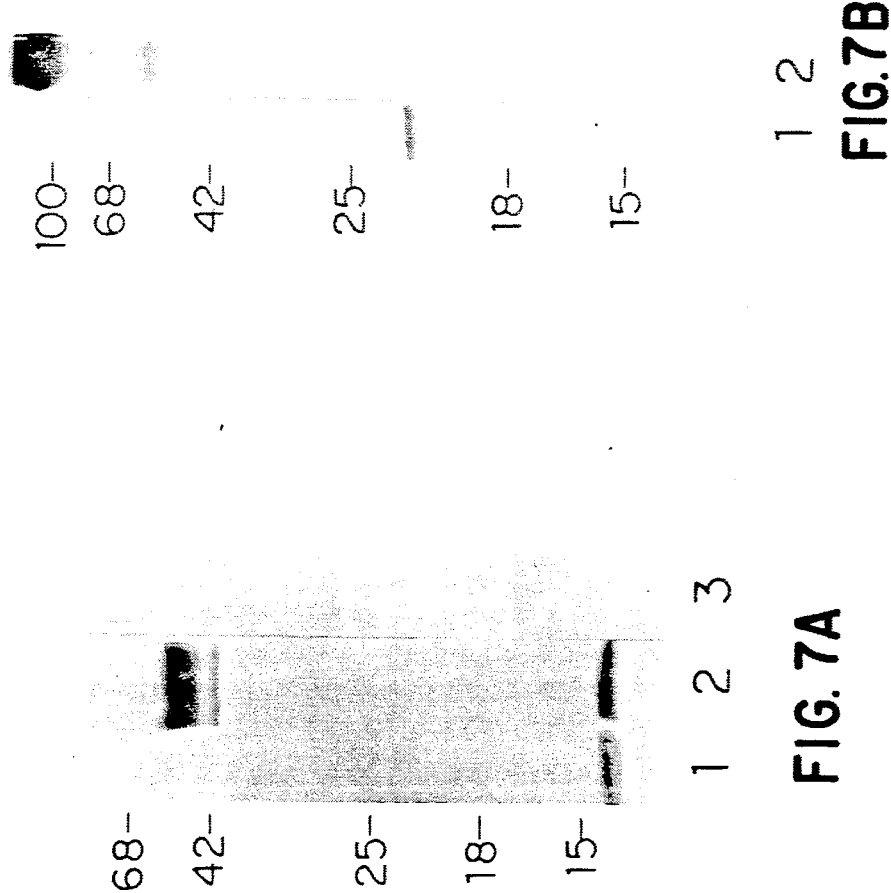

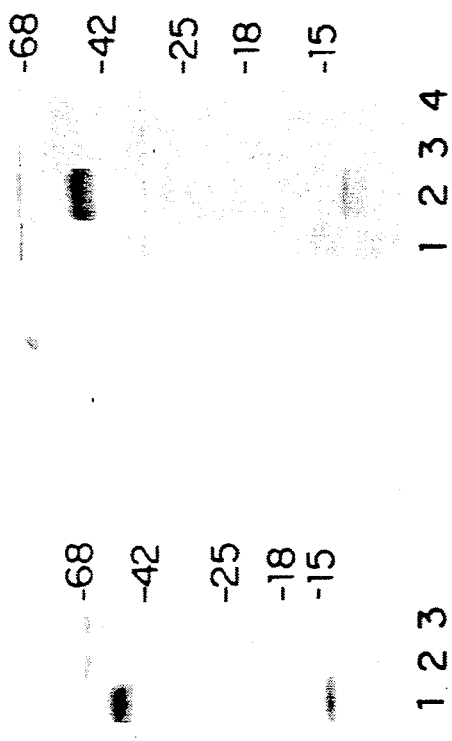

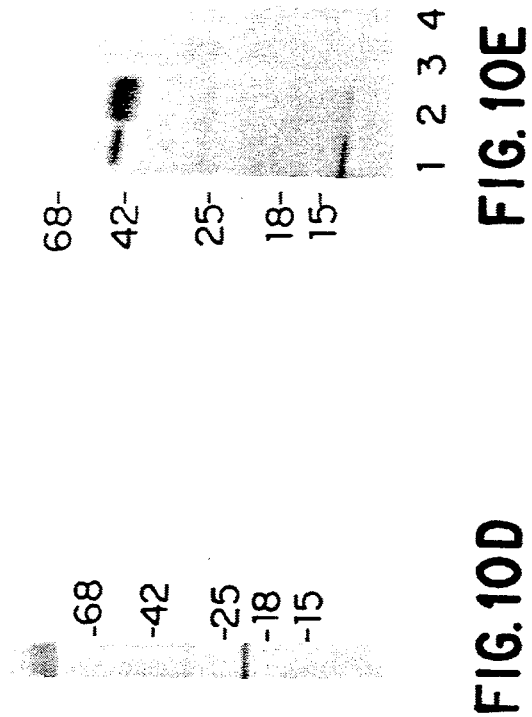

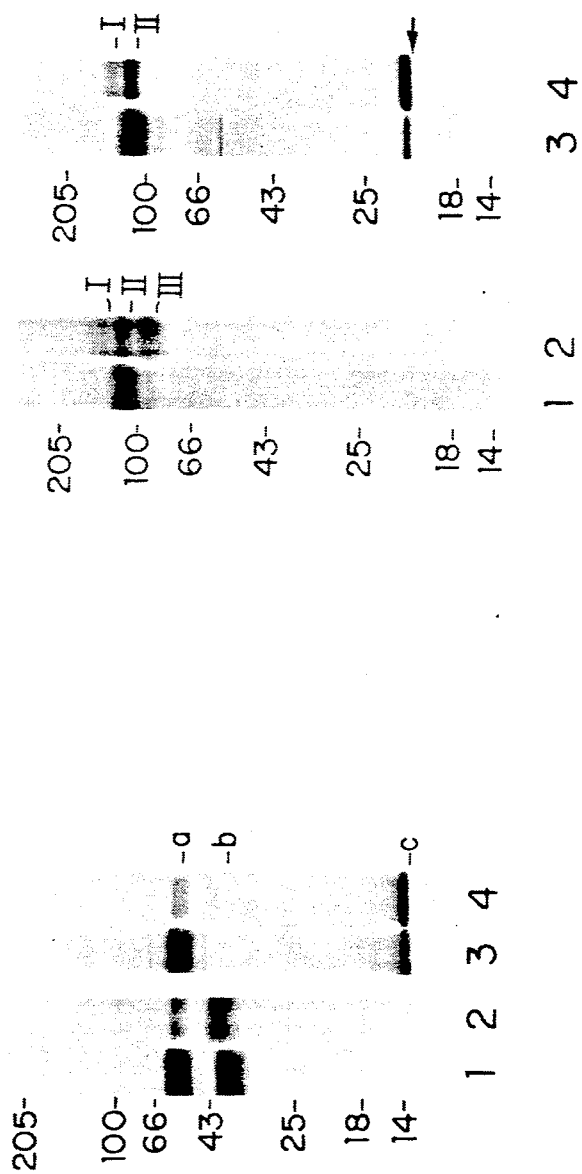

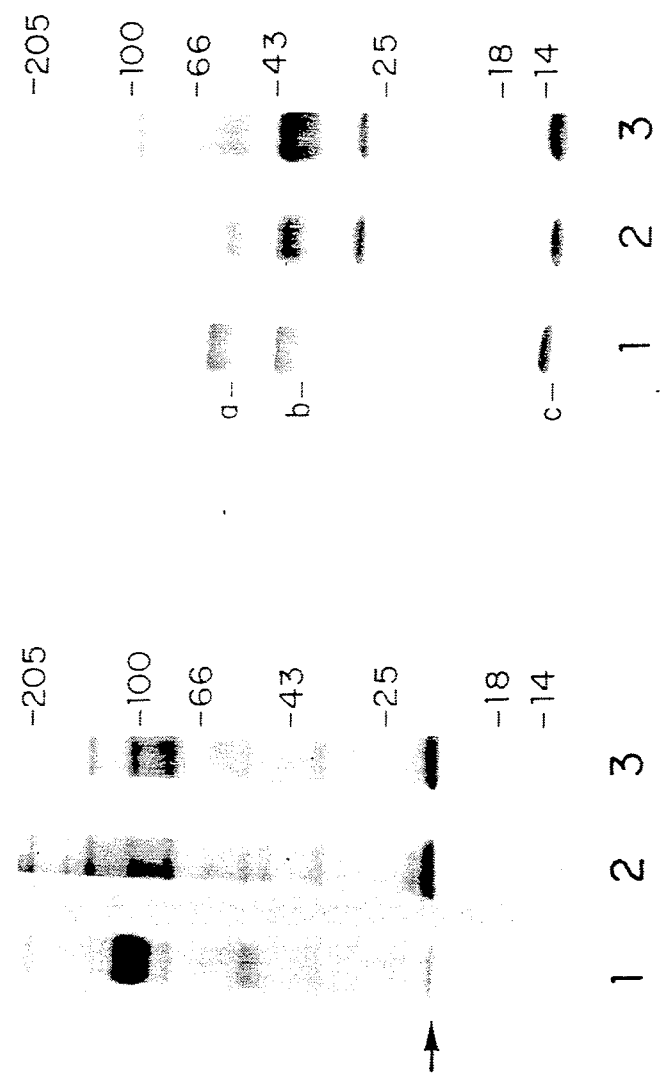

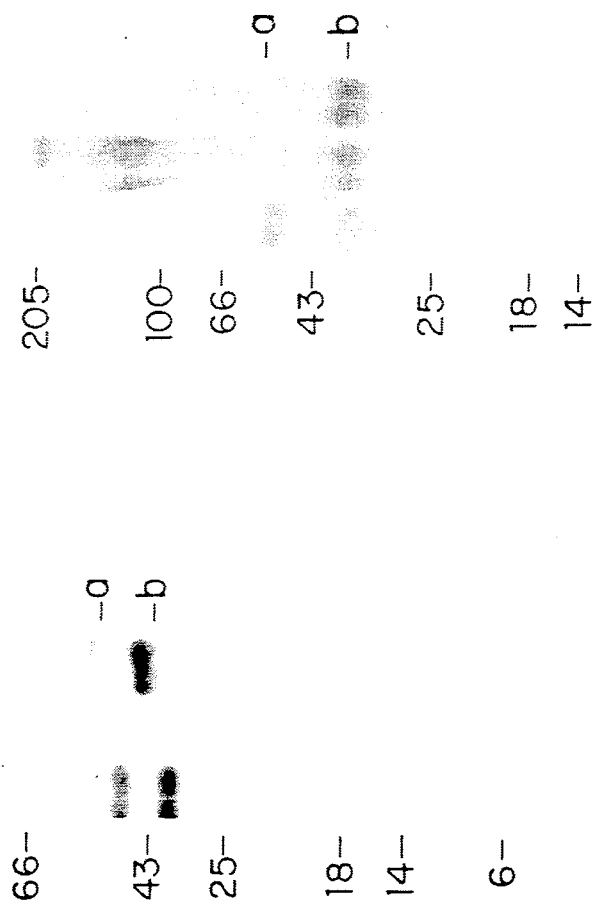

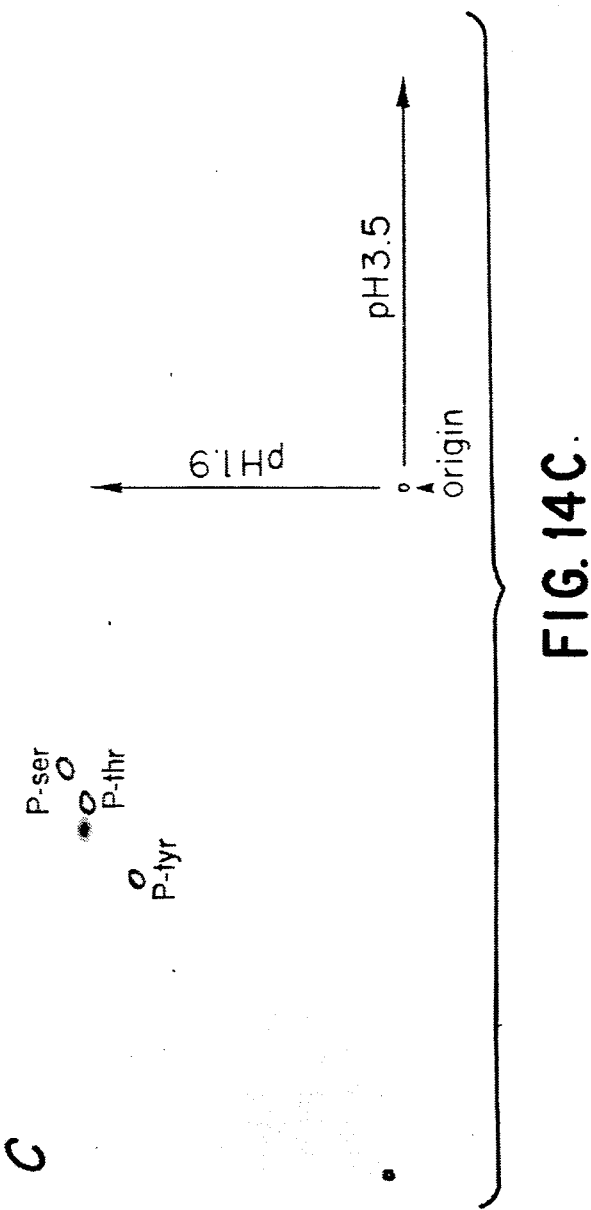

CLONING AND EXPRESSION OF TRANSFORMING GROWTH FACTOR β2

The present application is a continuation-in-part of copending application Ser. No. 07/285,140 filed Dec. 16, 1988 by Purchio et al., which is a continuation-in-part of application Ser. No. 234,065 filed Aug. 18, 1988 by Purchio et al., which is a continuation-in-part of copending application Ser. No. 148,267 filed Jan. 25, 1988 by Purchio et al., which is a continuation-in-part of copending application Ser. No. 106,752 filed Oct. 6, 1987 by Purchio et al., each of which application is abandoned and incorporated in its entirety by reference herein.

TABLE OF CONTENTS

1. Introduction
2. Background of the Invention
3. Summary of the Invention
  3.1. Definitions
4. Brief Description of the Figures
5. Description of the Invention
  5.1. Isolation or Generation of The TGF-β2 Coding Region
  5.2. Construction of Expression Vectors Containing the TGF-β2 Coding Sequence
  5.3. Identification of Transfectants or Transformants Expressing the TGF-β2 Gene Product
  5.4. Stable Expression of TGF-β2 in COS Cells
  5.6. Stable High-Level Expression of TGF-β2 in CHO Cells Using a TGF-β2(414) Precursor Gene
6. Example: cDNA Cloning of TGF-β2 Precursor From PC-3 Cells
  6.1. Materials and Methods
    6.1.1. Growth of Cells and RNA Extraction
    6.1.2. cDNA Library Construction and Screening
  6.2. Results
7. Example: cDNA Cloning of TGF-β2 Precursor From BSC-40 Cells
  7.1. Material and Methods
    7.1.1. Growth of cells and RNA Extracting
    7.1.2. cDNA Library Construction and Screening
  7.2. Results
8. Example: Expression of TGF-β2 in CHO Cells
  8.1. Materials and Methods
    8.1.1. Cell Structure
    8.1.2. DNA Manipulations and Plasmid Construction
    8.1.3. DNA Transfections
    8.1.4. Selection of Methotrexate Resistant Cells
    8.1.5. Growth Inhibition Assay
    8.1.6. Purification and Sequence Analysis of Recombinant Proteins
    8.1.7. Peptide Synthesis and Production of Antibodies
    8.1.8. Immunoblotting
    8.1.9. Receptor Binding Assay
  8.2. Construction of TGF-β1/TGF-β2 Hybrid Precursor Gene for TGF-β2 Expression
  8.3. Expression of TGF-β2 in CHO Cells
9. Example: Expression of TGF-β2 in COS cells
    9.1.1. Cell Culture
    9.1.2. Plasmid Constructions and COS Cell Transfections
    9.1.3. Analysis of Recombinant Proteins
  9.2. Results
10. Example: High-Level Expression of Simian TGF-β2 and the 414 Amino Acid Simian TGF-β2 Precursor in Chinese Hamster Ovary Cells
  10.1. Materials and Methods
    10.1.1. Cell Structure
    10.1.2. DNA Manipulations and Plasmid Constructions
    10.1.3. DNA Transfections and Selection of Methotrexate Resistant Cells
    10.1.4. Northern Blot Anaylsis
    10.1.5. Analysis of Secreted Proteins by PAGE and Two Dimensional Electrophoresis
    10.1.6. Immunoblot Analysis and Anti-Peptide Antibodies
    10.1.7. Growth Inhibition Assay
    10.1.8. Purification and Sequence Analysis of Recombinant Proteins
  10.2. Results
    10.2.1. Recombinant TGF-β2 Is secreted in a Latent Form
    10.2.2. Analysis of Recombinant TGF-β2 Proteins Secreted by Transfected CHO Cells
    10.2.3. Glycosylation and Phosphorylation of Pro-Region rTGF-β2 Precursor
    10.2.4. Purification and Sequence Analysis of Mature Recombinant TGF-β2
11. Deposit of Microoraganism

1. INTRODUCTION

The present invention relates to the cloning and expression of Transforming Growth Factor-β2.

2. BACKGROUND OF THE INVENTION

The Transforming Growth Factor-Beta (TGF-β) are members of a recently described family of polypeptides that regulate cellular differentiation and proliferation. Other members of this family include Mullerian inhibitory substance (Cate et al., 1986, Cell 45:685–698), the inhibins (Mason et al., 1985, Nature 318:659–663) and a protein predicted from a transcript of the decapentaplegic gene complex of Drosophila (Padgett et al., 1987, Nature 325:81–84).

Transforming Growth Factor-β1 (TGF-β1) is a 24,000 kD homodimer consisting of two identical disulfide bodned 112 amino acid subunits TGF-β1 was first described for its ability to stimulate the anchorage-independent growth of normal rat kidney fibroblasts (Roberts et al., 1981, Proce. Natl. Acad. Sci. U.S. A. 78:5339–5343),. Since then it has been shown to be a multi-functional regulator of cell grwoth and differentiation (Sporn et al., 1986, Science 233:532–534) being capable of such diverse effects of inhibiting the growth of several human cancer cell lines (Robers et al., 1985, Proc. Natl. Acad. Sci. U.S.A. 82:119–123; Ranchalis et al., 1987, Biochem. Biphys. Res. Commun.148:7-83–789), mouse keratinocytes (Coffey et al., 1988, Cancer Res. 48:1596–1602; Reiss and Dibble, 1988, In Vitro Cell. Dev. Biol. 24:537–544), and T and B lymphocytes (kehrl et al., 1986, J. Exp. Med. 163:1037–1050; 1987, J. Immunol. 137:3855–3860; Kasid et al., 1988, J. Immunol. 141:690–698; Wahl et al., 1988, J. Immunol 140:3026–3032). It also inhibits early hematopoietic progenitor cell proliferation (Goey et al., 1989, J. Immunol. 143:877–880), stimulates the induction of differentiation of rat muscle mesenchymal cells and subsequent production of cartilage-specific macromolecules (Seyedin et al., 1986, J. Biol. Chem. 262:1946–1949), causes increased synthesis and secretion of fibronectin and collagen (Ignotz and Massaque, 1986, J. Biol. Chem. 261:4337-4345; Centrella et al., 1987, J. Biol. Chem. 262:2869-2874), stimulates bone formation (Noda and Camilliere, 1989, Endocrinology 124:2991-2995), and accelerates the healing of incisional wounds (Mustoe et al., 1987, Sciene 237:1333-1335).

cDNA clones coding for human (Derynck et al., 1985, Nature 316:701-705), mouse (Derynck et al., 1986, J. Biol. Chem. 261:4377-4379) and simian (Sharples et a., 1987, DNA 6:239-244) TGF-β1 have been isolated. DNA sequence analysis of these clones indicates that TGF-β1 is synthesized as a large precursor polypeptide, the carboxy terminus of which is cleaved to yield the mature TGF-β1 monomer. Strong sequence homology has been found throughout the TGF-β1 precursor protein from all of the above sources.

TGF-β1 has been expressed to high levels in CHO cells (Gentry et al., 1987, Mol. Cell. Biol. 7:3418-3427). Analysis of proteins secreted by these cells by immunoblotting using site-specific anti-piptide antiserum together with protein sequencing of HPCL purified cyanogen bromide fragments indicated that recombinant TGF-β1 (rTGF-β1) is secreted as part of a high molecular weight latent complex composed of mature TGF-β1 non-covalently bound to a 90–110 kD sulfide linked complex consisting of mature and pro-region specific sequences (Gentry et al., 1987, Mol. Cell. Biol. 7:3418-3427; Gentry et al., 1988, Mol. Cell. Biol. 8:4162-4168). Similar structures have been described for rTGF-β1 secreted by human 293S cells. (Wakefield et al., 1989, Growth Factors 1:203-218).

Analysis of serum- and cell-free supernatants conditioned by recombinant CHO cells radiolabeled with [$^3$H]-glucosamine and [$^{32}$P]-orthophosphate indicated that the pro-region of the TGF-β1 precursor is phosphorylated and glycosylagted (Brunner et al., 1988, Mol. Cell. Biol. 8:2229-2232). Further analysis showed that the phosphate is incorporated as mannose-6-phosphate (M-6-P) and that this modification occurs at two of three glycosylation sites within the pro-region (Purchio et al., 1988, J. Biol. Chem. 263:14211-14215). Specific binding of the TGF-β1 precursor to the M-6-P receptor has been demonstrated (Purchio et al., 1988, J. Biol. Chem. 263:14211-14215; Kovacina et al., 1989, Biochem. Biophys. Res. Commun. 160:393-403).

Recently, a second protein termed Transforming Growth Factor-β2 (TGF-β2) was isolated from several sources including demineralized bone (Seyedin et al., 1987, J. Biol. Chem. 262:1946-1949), a human prostatic adenocarcinoma cell line (Ikeda et al., 1987, Biochemistry 26:2406-2410), a human glioblastoma cell line (Wrann et al., 1987, EMBO, J. 6:1633-1636) and procine platelets (Cheifetz et al., 1987, Cell 48:409-415). Complete amino acid sequence of TGF-β2 shows 71% homology with TGF-β1 (Marquardt et al., 1987, J. Biol. Chem. 262:12127-12131) and it shares several functional similarities with TGF-β1 (Ranchalis et al., 1987, Biochem. Biophys. Res. Commun. 148:783-789; Seyedin et al., 1987, J. Biol. Chem. 262:1946-1949; McPherson et al., 1989, Biochemistry 28:3442-3447). These proteins are now known to be members of a family of related growth modulatory proteins including TGF-β3 (Ten-Dijke et al., 1988, Proc. Natl. Acadm Sci. U.S.A. 85:4715-4719; Derynck et al., 1988, EMBO J. 7:3737-3743; Jakowlew et al., 1988a, Mol. Endocrinol. 2:747-755), TGF-β4 (Jakowlew et al., 1988B, Mol. Endocrinol. 2:1064-1069), Mullerian inhibitory substance (Cate et al., 1986, Cell 45:685-698) and the inhibins (Mason et al., 1985, Nature 318:659-663).

3. SUMMARY OF THE INVENTION

The present invention relates to the production of large quantities of TGF-β2 by eukaryotic host cells transfected with recombinant DNA vectors containing a TGF-β2 coding sequence controlled by expression regulatory elements.

In a specific embodiment, cDNA clones coding for human TGF-β2 precursor were obtained from a cDNA library made from a tamoxifen treated human prostatic adenocarcinoma cell line PC-3. The cDNA sequence of one such clone predicts that TGF-β2 is synthesized as a 442 amino acid polypeptide precursor from which the mature 112 amino acid TGF-β2 subunit is derived by proteolytic cleavage. This TGF-β2 precursor, termed TGF-β2-442, shares a 41% homology with the precursor of TGF-β1. In another embodiment, cDNA clones coding for simian TGF-β2 precursor were obtained from a cDNA library made from an African green monkey kidney cell line, BCS-40. The cDNA sequence of one such clone predicts that TGF-β2 is also synthesized as a 414 amino acid polypeptide precursor from which the mature 112 amino acid TGF-β2 subunit is derived by proteolytic cleavage. This TGF-β2 precursor, termed TGF-β2-442, has an amino acid sequence of 414 amino acids residues and is identical to the amino acid sequence of TGF-β2-442, except that it contains a single Asparagine residue instead of the 29 amino acid sequence from residue numbers 116 to 135 of the human TGF-β2-442 sequence.

Clones from the BSC-40 cDNA library which encode a simian TGF-β2-442 precursor as well as clones from the human PC-3 cDNA library which encode a human TGF-β2-414 precursor have also been identified. The human and simian TGF-β2-442 precursors appear to be perfectly homologous at the amino acid level, as do the human and simian TGF-β2-414 precursors. The mature 112 amino acid monomers of TGF-β1 and TGF-β2 show 71% homology.

In another embodiment of the invention, described further by the examples herein, expression vectors containing the TGF-β2 mature coding sequence joined in-phase to the TGF-β1 signal and precursor sequences (Co-owned/pending U.S. patent application Ser. No. 189,984) were constructed and used to transfect Chinese Hamster Ovary cells (CHO cells) and COS cells. The resulting CHO and COS transfectants produce and secrete mature, biologically active TGF-β2. In a related embodiment, the complete simian TGF-β2-414 precursor gene was used to construct an expression vector which directs the high-level expression of both mature and precursor forms of TGF-β2 in transfected CHO cells.

3.1. DEFINITIONS

The following terms as used herein whether in the singular or plural, shall have the meanings designated.

TGF-β2: A transforming growth factor-Beta2 of human or simian origin comprising the amino acid sequence substantially as depicted in FIGS. 1B through 1C from about amino acid residue number 331 to about amino acid residue number 442.

TGF-β2 precursor: A family of transforming growth factor-Beta2 molecules of human or simian origin comprising an amino acid sequence substantially as depicted in FIGS. 1A through 1C from about amino acid residue number 1 to about amino acid residue number 442, or from about amino acid residue number 1 to about amino acid residue number 442 where the amino acid sequence from amino acid residue number 116 to amino acid residue number 144 is deleted and replaced by a single Asparagine residue. The term shall means a TGF-beta 2 precursor designated TGF-β2-442 or TGF-β2-414, whether of human or simian origin.

Hybrid TGF-β1/TGF-β2 precursor: A novel transforming growth factor-beta precursor molecule comprising the amino acids sequence substantially as depicted in FIGS. 1D through 1F from about amino acid residue number 1 to about amino acid number 390.

TGF-β1 precursor: Simian-transforming growth factor-Beta1 precursor and signal sequences substantially as depicted in FIG. 1b from about amino acid residue number 1 to about amino acid residue number 279.

BRIEF DESCRIPTION OF THE FIGURES

FIGS. 1A through 1C Nucleotide sequence of human TGF-β2-442 cDNA and deduced amino acid sequence. The 2597 bp insert of PC-21 was subcloned into pEMBL (Dante et al., 1983, Nucleic Acids Res. 11:1645-1654) and sequenced on both strands using the dideoxy chain-termination method (Sanger et al., 1977, Proc. Natl. Acad. Sci. USA 74:5463-5467). The coding sequence is shown and the deduced amino acid sequence is presented directly above. The mature TGF-β2 sequence is boxed and the signal peptide is overlined. Potential glycosylation sites are indicated by asterisks. The arrow indicates the putative signal sequence cleavage site. The nucleotide sequence of simian TGF-β2-414 cDNA is identical to the human. TGF-β2 -442 cDNA sequence except that nucleotides 346 through 432 (bracketed) are deleted and replaced by the sequence AAT, and except that several silent nucleotide changes occur elsewhere in the structure (indicated by single letters directly below the changed nucleotide). The deduced amino acid sequence for simian TGF-β2-414 precursor is identical to the human TGF-β2-442 precursor amino acid sequence except that Asparagin replaces amino acid residues 116 through 144 in the human TGF-β2-442 structure. The nucleotide sequence of a human TGF-β2-414 cDNA has been sequenced through the region indicated by broken underlining and was found to be perfectly homologous to the human TGF-β2-442 cDNA sequence except that nucleotides 346 through 432 are deleted and replaced by the sequence AAT.

FIGS. 1D through 1F Nucleotide sequence of hybrid TGF-β1/TGF-β2 precursor DNA and deduced amino acid sequence. The coding sequence is shown and the deduced amino acid sequence is presented directly above. The mature TGF-β2 sequence is boxed and the precursor signal peptide is overlined. Glycosylation sites are indicated by asterisks. The arrow indicates the putative signal sequence cleavage site. The TGF-β2 mature coding sequence depicted is a human origin. The simian TGF-β2 mature coding sequence is nearly identical to the human sequence; only 3 silent base changes occur and are indicated by single letters directly below the changed nucleotide. Details of the cDNA cloning of TGF-β2 and the construction of the hybrid TGF-β1/TGF-β2 gene are described in Section 8, infra.

FIG. 1G Schematic diagram of hybrid TGF-β1/TGF-β2 precursor gene.

FIG. 1H Restriction endonuclease maps of pPC-14 (2.2 kb) and pPC-21 (2.3 kb). The boxed region indicate coding sequences for TGF-β2 monomer. The ATG denotes the initiating methionine codon. The distance between the ATG and KpnI site in pPC-21 (2.34 kg) is approximately 420 bp. The darkened area indicates the position of the 84-bp insertion in pPC-21 (2.3 kb).

FIG. 1I Partial DNA sequence analysis of pPC-14 (2.2 kb). A synthetic oligonucleotide 5'-AGGAGC-GACGAAGAGTACTA-3' which hybridized approximately 140 bp upstream from the KpnI site within the insert of pPC-21 (2.3 kb) was used to prime DNA sequencing reactions. In this region, the sequence of pPC-14 (2.2 kb) (upper line) is identical to pPC-21 (2.3 kb) up to nucleotides coding for Asn-116. The 84-bp insertion within the Asn-116 codon of pPC-14 (2.2 kb) which was found in pPC-21 (2.3 kb) is shown. The KpnI site within the insert is denoted.

FIGS. 2A and 3B Homologies of human TGF-β1 and TGF-β2-442 precursor sequences. FIG. 2A Primary sequence homology: identical residues are boxed. Asterisks refer to potential glycosylation sites in TGF-β2. The potential signal sequence cleavage site and the cleavage site of the mature polypeptide are indicated.

FIGS. 3A and 3B Northern blot analysis of BSC-40 and PC-3 polyadenylated RNA. Polyadenylated RNA was isolated from BSC-40 and PC-3 cells, fractionated on a agarose-formaldehyde gel, transferred to hybond-N filters and hybridized to [$^{32}$P]-labeled TGF-β2 specific probe, pPC-21 FIG. 3A or a mixture of [$^{32}$P]-labeled TGF-β2 and TGF-β1 (Sharples et al., 1987) specific probes FIG. 3B. Lane 1, BSC-40 polyadenylated RND (5 micrograms); lane 2, PC-3 polyadenylated RNA (5 micrograms).

FIGS. 7A and 7B Characterization of recombinant proteins secreted by amplified, transfected CHO cells. FIGS. 7A Serum-free supernatant collected from 1β9, 12.5 CL36 was analyzed by immunoblotting with anti-TGF-β2$_{395-407}$ (lane 2) or with anti-TGF-β2$_{395-407}$ that had been incubated with excess peptide prior to immunoblotting (lane 3). Lane 1 contains natural TGF-β2 (Marquardt et al., 1987, J. Biol. Chem. 262:12127-12131). Samples were fractionated on a linear 15% polyacrylamide-SDS gel under reducing conditions. FIG. 7B: 1β9, 12.5 CL36 conditioned media (lane 2) and natural TGF-β2 (lane 1) were fractionated on a 7.5-15% polyacrylamide-SDS gel and immunoblotted with anti-TGF-β2$_{395-407}$. Gels were run under non-reducing conditions.

FIGS. 8A, 8B and 8C Characterization of purified recombinant TGF-β2 (rTGF-β2) purified from serum-free media conditioned by 1β9, 12.5 CL36 cells. FIG. 8A: rTGF-β2 fractionated on a 15% polyacrylamide-SDS gel under non-reducing conditions and stained with silver. FIG. 8B: rTGF-β2 fractionated on a 7.5-15% gradient polyacrylamide-SDS gel under reducing (lane 1) and non-reducing (lane 2) conditions and detected by immunoblotting with anti-TGF-β2$_{395-407}$. FIG. 8C: Iodinated rTGF-β2 fractionated on a 7.5-15% gradient polyacrylamide-SDS gel under reducing (lane 1) and non-reducing (lane 2) conditions and detected by autoradiography.

FIGS. 1A through 10E. Characterization of recombinant proteins secreted by transfected COS cells. FIG. 10B: COS cells were transfected with pβ1'; 48 hr post transfection, media was replaced with serum-free media then collected 48 hours later. Samples were dialyzed against 0.2 M acetic acid, dried and assayed by immunoblotting under reducing conditions using anti-TGF-β1$_{369-381}$. Lane 1, COS cells+pβ1'; lane 2, COS cells +vector only (pπXH3M); lane 3, COS cells+PBS. FIG. 10C COS cells were transfected with pβ1' lane 1), pβ1/β2' (lane 2), pπXH3M (vector only, lane 3) and PBS (lane 4). Serum-free supernatants were collected 48 hours post-transfection and analyzed by immunoblotting under reducing conditions using anti-TGF-β2$_{395-407}$. FIG. 10D: COS cells were transfected with pβ1/β2' and supernatants were analyzed by immunoblotting under non-reducing conditions using anti-TGF-β2$_{395-407}$. FIG. 10E: COS cells were transfected with pβ2' (lane 1), pβ1/β2' (lane 2), pπXH3M vector only (lane 3), PBS (lane 4); serum-free supernatants were analyzed by immunoblotting conditions using anti-TGF-β2$_{395-407}$.

Numbers to the right (left in FIG. 10E) indicate positions of molecular weight standards in kilodaltons. Samples were fractionated on a 7.5-15% gradient (15% linear in FIG. 10C) polyacrylamide-SDS gel.

Figure 11A:
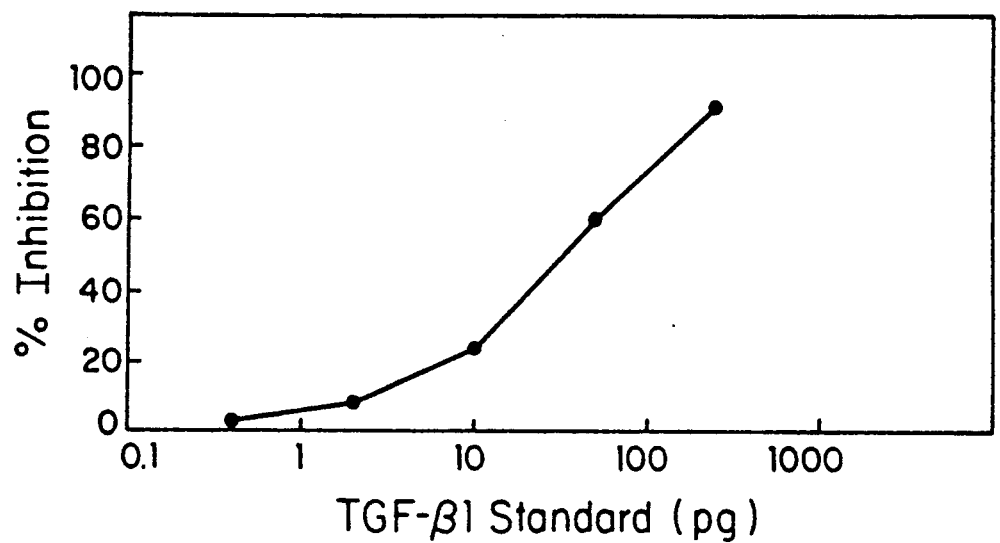
Figure 11B:
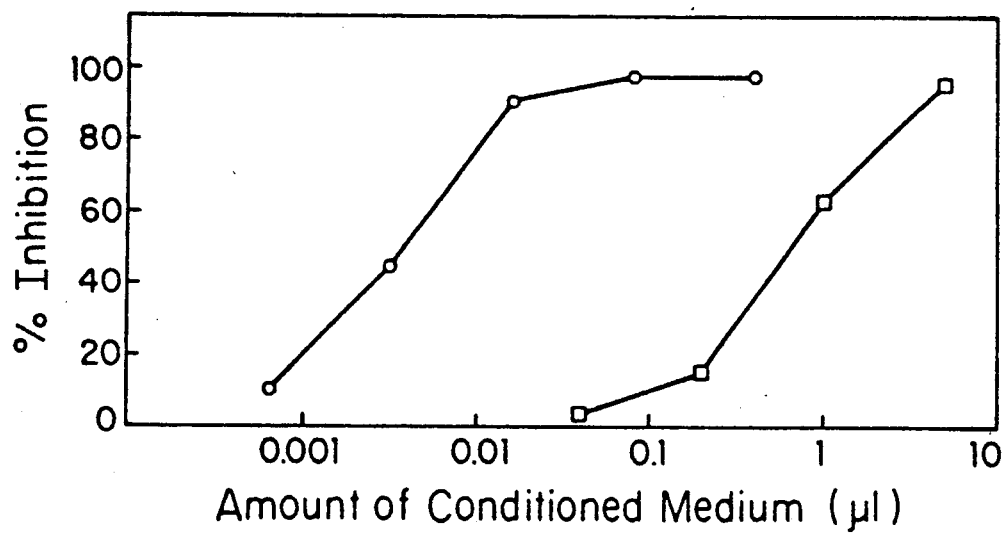
Figure 11C:
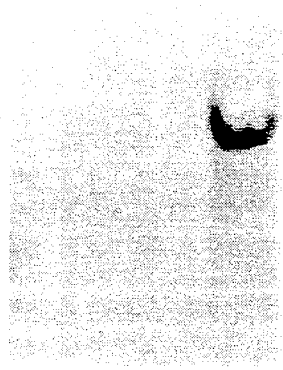

FIGS. 11A and 11B and 11C Growth inhibition of mink lung cells with rTGF-β1 and rTGF-β2. FIG. 11A: rTGF-β1 was purified as described (Gentry et al., 1988, Mol. Cell. Biol. 8:4162-4168) and used in the growth inhibition assay described in Section 10.7.7., infra. FIG. 11B: β2(414)cl.32 cells were grown to confluency in 100 mm dishes. Cells were washed 3× with serum-free medium and incubated with 5 ml of serum-free medium for 24 hours. Media was collected, clarified at 2000 xg for 5 minutes, dialyzed against either 0.2 M acetic acid (o—o) or 50 mM NH$_4$HCO$_3$, pH 7.0 (—) and assayed for growth inhibition of milk lung cells. FIG. 11C: Total RNA was extracted from bnormal CHO cells (lane 1) or β2(414)cl.32 cells (lane 2); 30 μg of total RNA was fractionated on an agarose-formaldehyde gel, transferred to a nylon membrane and probed with a [$^{32}$P]-labeled TGF-β2 specific probe (pPC-21(2.3 kb) as described in Section 10.1.4., infra.

Figure 12A:
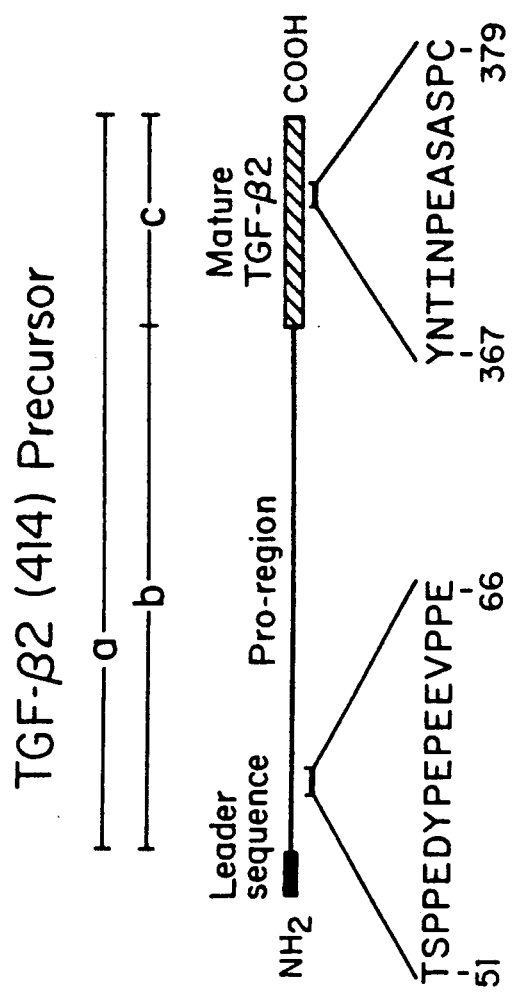

FIGS. 12A through 12E. Detection of TGF-β2 specific proteins by immunoblotting and direct metabolic labeling. FIG. 12A: Line diagram of the TGF-β2 precursor showing the peptide sequences against which anti-peptide antibodies were made. 'a' denotes the pro-TGF-β2-414 region; 'b' denotes the pro-region of the TGF-β2-414 precursor and 'c' denotes the TGF-β2 monomer. FIG. 12B: Serum- and cell-free media condition by β1cl.17 cells (lanes 1 and 3) or β2(414)cl.32 cells (lanes 2 and 4) were fractionated by SDS-PAGE under reducing conditions and analyzed by immunoblotting using anti-TGF-β1$_{81-94}$ (lane 1), anti-TGF-β2(414)$_{51-66}$ (lane 2), anti-TGF-β1$_{369-381}$ (lane 3) or anti-TGF-β2(414)$_{367-379}$ (lane 4). FIG. 12 C: Serum- and cell-free media conditioned by β1cl.17 cells (lanes 1 and 3) or β2(414)cl.32 cells (lanes 2 and 4) were fractionated by SDS-PAGE under non-reducing conditions and analyzed by immunoblotting using anti-TGF-β1$_{81-94}$ (lane 1), anti-TGF-β2(414)$_{51-66}$ (lane 2), anti-TGF-β1$_{369-381}$ (lane 3) or anti-TGF-β2(414)$_{367-379}$ (lane 4). FIG. 12D: β1cl.17 cells (lane 1), β2(414)cl.32 cells (lane 2) and β2(414)cl. 35 cells (lane 3) were labeled with [$^{35}$S]-methionine plus [$^{35}$S]-cysteine and serum-free supernatants were analyzed by SDS-PAGE on a 7.5-17.5% gel under non-reducing conditions. FIG. 12E: β1cl.17 cells (lane 1), β2(414)cl.32 cells (lane 2) and β2(414)cl.35 cells (lane 3) were labeled with [$^{35}$S]-methionine plus [$^{35}$S]-cysteine and serum-free supernatants were analyzed by SDS-PAGE on a 7.5-17.5% gel under reducing conditions.

FIGS. 13A and 13B. Analysis of [$^{32}$P]-orthophosphate [$^3$H]-glucosamine labeled proteins secreted by recombinant CHO cells. FIG. 13A: Confluent β1cl.17 cells (lane 1) or β2(414)cl.32 cells (lane 2) were labeled for 4 hours with 1 mCi/ml [$^{32}$P]-orthophosphate: serum- and cell-free supernatants were dialyzed against 0.2 M acetic acid and analyzed by SDS-PAGE on a 15% gel under reducing conditions. Alternatively, in FIG. 13B, confluent β1cl.17 cells (lane 3), β2(414)cl.32 cells (lane 4) and β2(414)cl.35 cells (lane 5) were labeled with [$^3$H]-glucosamine and serum and cell-free supernatants were analyzed by SDS-PAGE on a 7.5-17.5% gel under reducing conditions.

Figures 14A, 14B:

FIGS. 14A, 14B and 14C. Indentificaion of mannose-6-phosphate within the pro-region of TGF-β2-414. FIG. 14A: Confluent β1cl.17 cells were labeled with [$^{32}$P]-orthophosphate and cell- and serum-free supernatants were fractionated by SDS-PAGE. Bands 'a' and 'b' from lane 1, FIG. 13A, were isolated, hydrolyzed in 6M HCl and fractionated by two-dimensional electrophoresis as described (Cooper et al., dimensional electrophoresis as described (Cooper et al., 1983, Method Enzymol. 99:387–402). The position of migration of M-6-P located within the TGF-β1 pro-region (Purchio et al., 1988, J. Biol. Chem. 263:14211-14215) is indicated. FIG. 14B: Confluent β1(414)cl.32 cells were labeled with [$^{32}$P]-orthophosphate and serum- and cell-free supernatants were fractionated by SDS-PAGE. Band 'b' from lane 2, FIG. 13AS, was isolated, hydrolyzed in 6M HCl and fractionated by two-dimensional electrophyoresis. FIG. 14C: Mix of A and B. Equivalents cpm from A and B were used.

Figure 15:
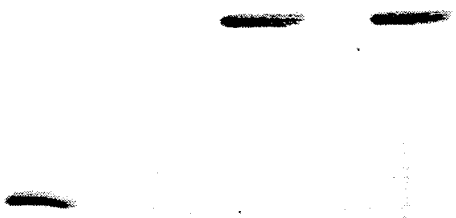

FIG. 15. Analysis of purified rTGF-β2. rTGF-β2 was purified from media conditioned by β2(414)cl.32 cells and 1 μg was fractionated by SDS-PAGE on a 7.5–17.5% gel under reducing (lane 1) or non-reducing (lane 2) conditions. The gel was stained with Comassie blue. Lane 3 contains 1 μg of rTGF-β1 (non-reduced).

5. DESCRIPTION OF THE INVENTION

The present invention relates to the production of a biologically active, mature form of TGF-β2 from a TGF-β precursor gene coding sequence and its product. The mature bilogicaslly active TGF-β2 may be produced by the cloning and expression of the full-length nucleotide coding sequence of the TGF-β2 precursor or its functional equivalent in a host cell which processes the precursor correctly so that a mature TGF-β2 is produced having a biological activity that is virtually indistinguishable from that of authentic natural TGF-β2. Functional equivalents of the full length nucleotide coding sequence of the TGF-β2 precursor include any DNA sequence which, when expressed inside an appropriate host cell, is capable of directing the synthesis, processing and export of mature TGF-β2. In this regard, hybrid precursor coding sequences including, for example, the TGF-β1 precursor sequence joined in-frame to the TGF-β2 mature sequence, may be constructed and used to produce biologically active TGF-β2.

Similarly, the present invention also relates to the production of precursor forms of TGF-β2 by eukaryotic host cells transfected with vectors encoding the complete TGF-β2 precursor coding sequence, including latent high molecular weight TGF-β2 precursor complex, the pro region of TGF-β2, and unprocessed TGF-β2 precursor.

The method of the invention may be divided into the following stages solely for the purposes of description: (a) isolation or generation of the coding sequence for a precursor form of TGF-β2; (b) construction of an expression vector which will direct the expression of a TGF-β2 coding sequence; (c) transfection of appropriate host cells which are capable of replicating and expressing the gene and processing the gene product to produce the matrue, bilogically active form of TGF-β2 or, alternatively, latent TGF-β2 precursor forms; and (d) identification and purification of the mature, biologically active TGF-β2 or latent TGF-β2 precursor forms. Once a transfectant is identified that expresses high levels of TGF-β2, the practice of the invention involves the expansion of that clone and isolation of the gene product expressed.

The method of the invention is demonstrated herein, by way of examples in which cDNAs of the TGF-β2 precursor coding region were prepared, cloned, sequenced, and utilized to construct expression vectors capable of directing high-level expression of TGF-β2 in mammalian host cells. In a specific embodiment, applicants have identified clones from a PC-3 cDNA library coding for TGF-β2. DNA sequence analysis of one of these clones revealed that TGF-β2, like TGF-β1, is synthesized as a larger precursor protein, the carboxy terminus of which is cleaved to yield the mature TGF-β2 monomer. While there is a 71% homology between TGF-β1 and TGF-β2 throughout the mature portions of these molecules, only a maximum of 31% homology exists within the rest of the precursor, suggesting that the amino terminal regions of TGF-β1 and TGF-β2 may be functionally distinct.

In a specific embodiment of the invention, expression of a novel TGF-β1/TGF-β2 hybrid gene in CHO cells is used to produce large amounts of biologically active TGF-β2. In yet another embodiment, mature and precursor forms of TGF-β2 are obtained from CHO cells engineered to express at high levels the complete TGF-β2 precursor coding sequence. Applicants have determined, and describe herein, various biochemical, immunological, and structural characteristics of the recombinant TGF-β2 proteins secreted by these cells.

The various aspects of the method of the invention are described in more detail in the subsections below and in the examples that follow.

5.1 ISOLATION OR GENERATION OF THE TGF-β2 CODING REGION

The nucleotide coding sequence for TGF-β2 is depicted in FIG. 1a. In the practice of the method of the invention, the nucleotide sequence depticted therein, or fragments or functional equivalents thereof, may be used to generate the recombinant moleculres which will direct the expression of the TGF-β2 product in appropriate host cells. In a specific embodiment, described further in Section 10., infra, the high level expression of TGF-β2 and the 414 amino acid TGF-β2 precursor is achieved in Chinese Hamster Ovary cells transfected with a recombinant plasmid encoding simian TGF-β2(414) precursor and dihydrofolate reductase (DHFR) under the regulatory control of the SV-40 promotor. Subsequent amplification of expression with methotrexate results in the isolation of clones secreting high levels of matrue TGF-β2 as well as high-molecular weight precursor complexes. These clones secrete approximately 5 μg recombinant TGF-β2 per ml culture media. Preliminary characterization of the secreted TGF-β2 precursor indicates that its pro-region is glycosylated and contains mannose-6-phosphate. In another, related embodiment, a TGF-β1/TGF-β2 hybrid gene was constructed and used to transfect CHO cells; the resulting transfectants secrete as much as 0.4 μg recombinant TGF-β2 per ml culture media.

Due to the degeneracy of the nucleotide coding sequences, other DNA sequences which encode substantially the same amino acid sequences as depicted in FIGS. 1A through 1C FIGS. 1D through 1F may be used in the practice of the present invention for the cloning and expression of TGF-β2. Such alterations include deletions, additions or substitutions of different nucleotide residues resulting in a sequence that encodes the same or a functionally equivalent gene product. The gene product may contain deletions, additions or substitutions of amino acid residues within the sequence, which result in a silent change thus producing a bioactive product. Such amino acid substitutions may be made on the basis of similarity in polarity, charge, solubility, hydrophobicity, hydrophilicity and/or the amphipathic nature of the resides involved. For example, negatively charged amino acids include aspartic acid and glutamic acid; positively charged amino acids include lysine and arginine; amino acids with uncharged polar head groups or nonpolar head groups having similar hydrophilicity values include the following: leucine, isoleucine, valine; glycine, alanine; asparagine, glutamine, serine, threonine, phenylalanine, tyrosine.

The nucleotide coding sequence of TGF-$\beta$2 may be obtained from cell sources that produce TGF-$\beta$2 like activity. The coding sequence may be obtained by cDNA cloning of RNA isolated and purified from such cellular sources or by genomic cloning. Either cDNA or genomic libraries of clones may be prepared from the DNA fragments generated using techniques well known in the art including but not limited to the use of restriction enzymes. The fragments which encode TGF-$\beta$2 may be identified by screening such libraries with a nucleotide probe that is substantially complementary to any portion of the sequence depicted in FIGS. 1A-1C. Full length clones, i.e., those containing the entire coding region for the TGF-$\beta$2 precursor may be selected for expression.

In an alternate embodiment of the invention, the coding sequences of FIGS. 1A-1C could be synthesized in whole or part, using chemical methods well known in the art. See, for example, Caruthers et al., 1980, Nuc. Acids Ses. Symp. Ser. 7:215-233; Crea and Horn, 1980, Nuc. Acids. Res. 9(10):2331; Matteucci and Carruthers, 1980, Tetrahedron Letters 21:719 and Chow and Kempe, 1981, Nuc. Acids, Res. 9(12):2807-2817. Alternatively, the protein could be produced using chemical methods to synthesize the amino acid sequence depicted in FIGS. 1A-1C in whole or in part. For example, peptides can be synthesized by solid phase techniques on a Beckman 990 instrument, and cleaved from the resin as previously described (Gentry, L. E., et al., 1983), J. Biol. Chem. 258:11219-11228; Gentry, L. E. and Lawton, A., 1986, Virology 152:421-431). Purification can be accomplished by preparative high performances liquid chromatography. The composition of the peptides may be confirmed by amino acid analysis.

In a specific embodiment, described further in Section 6., infra, the TGF-$\beta$2 coding sequence may be obtained by cDNA cloning of human TGF-$\beta$2 precursor coding sequences derived from polyadenylated RNA isolated from tamoxifen-treated human prostatic adenocarcinoma cell line, PC-3, previously shown to produce TGF-$\beta$2. Similarly, in a related embodiment further described in Section 7., infra, the TGF-$\beta$2 coding sequence may be obtained by cDNA cloning of simian TGF-$\beta$2 precursor coding sequences derived from polyadenylated RNA isolated from an African green monkey cell line, BSC-40. The human and simian TGF-$\beta$2 precursors appear to have identical amino acid sequences, and their nucleotide sequences are nearly identical.

DNA sequence analysis or TGF-$\beta$2 cDNA clones indicates that TGF-$\beta$2, like TGF-$\beta$1, is synthesized as a large precursor protein, the carboxy terminus of which is cleaved to yield the mature 112 amino acid TGF-$\beta$2 monomer. TGF-$\beta$2 has been shown to have a molecular weight of 24,000 composed of two disulfide-linked 13,000 dalton subunits (Ikeda et al., 1987, Biochemistry 26:2406-2410; Cheifetz et al., 1987, Cell 48:409-415). Therefore, the production of mature TGF-$\beta$2 requires proper proteolytic cleavage as well as the formation of intra- and inter-molecular disulfide bonds. An amino terminal hydrophobic leader sequence (residue 3-19) is present in the precursor and may be responsible for directing the protein out of the cell. The mature TGF-$\beta$2 may still be associated with the remaining portion of the precursor during this process.

TGF-$\beta$2 shows 71% homology with TGF-$\beta$1 throughout the mature portion of the precursor, implying a functional similarity which is supported by experimental evidence (Seyedin et al., 1987, J. Biol. Chem. 262:1946-1949; Cheifetz et al., 1987, Cell 48:409-415). The amino portion of the precursor region of TGF-$\beta$1 from human, rodent and simian sources (Derynck et al., 1985, Nature 316:701-705; Derynck et al., 1986, J. Biol. Chem. 261:4377-4379; Sharples et al., 1987, DNA 6:239-244) is highly conserved and suggests that his part of the molecule may have an important biological function. In contrast, there is no more than 31% homology between the N-terminal precursor regions of TGF-$\beta$1 and TGF-$\beta$2. After cleavage of the putative signal peptide, the TGF-$\beta$2 precursor would also contain more amino acids than TGF-$\beta$1 precursor. The primary structural differences within the amino terminal region of the TGF-$\beta$1 and TGF-$\beta$2 precursor proteins may reflect functional differences. However, significant homologous regions within the precursors are found in isolated blocks suggesting the conservation of important functional domains even within the N-terminal precursor region.

Northern bloc analysis revealed two major size classes of TGF-$\beta$2-specific mRNA of 4.1 and 6.5 kb in BSC-40 cells. Tamoxifen-treated PC-3 cells contain three TGF-$\beta$2 transcript of 4.1 kb, 5.1 kb, and 6.5 kb. These different-sized messages could be the result of differential RNA splicing, polyadenylation, or both as has been described for other genes (Helfman et al., 1986, Mol. Cell. Biol. 6:3582-3595; Sayre et al., 1987, Proc. Natl. Acad. Sci. USA 84:2941-2945). Preliminary analysis of another TGF-$\beta$2 cDNA clone shows that it contains a 3'-untranslated region approximately 1 kb larger than that of pPC-21 and pPC-14 and contains a different polyadenylation site suggesting that alternative polyadenylation is one factor responsible for the generation of multiple TGF-$\beta$2 mRNAs observed on Northern blots.

Figures 3A, 3B:
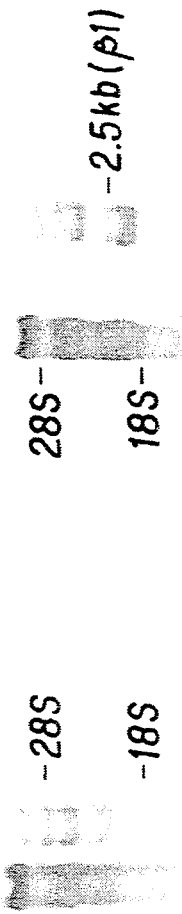

BSC-40 cells contain comparable levels of TGF-$\beta$1 and TGF-$\beta$2-specific transcripts: tamoxifen-treated PC-3 cells contain more TGF-$\beta$1 mRNA than TGF-$\beta$2 (FIG. 3B). The latter result is unexpected since these cells produce more TGF-$\beta$2 protein than TGF-$\beta$1 (Ikeda et al, 1987, Biochemistry 26:2406-2410) and suggests a post-transcriptional level of regulation regarding the synthesis of this growth modulator. Production of adequate amounts of TGF-$\beta$2 by recombinant DNA techniques, as has been done for TGF-$\beta$1, should aid further in designing experiments to explore the different effects of this protein.

5.2 CONSTRUCTION OF EXPRESSION VECTORS CONTAINING THE TGF-$\beta$2 CODING SEQUENCE In order to express a bilogically active, mature form of TGF-$\beta$2, an expression vector/host system should be chosen which provides not only for high levels of transcription and translation but for the correct processing of the gene product. This is especially important when employing the entire coding sequence of a TGF-$\beta$2 precursor in the expression constructs because the mature form of TGF-$\beta$2 appear to be derived from the precursor product via cellular processing events. In addition, an expression/host cell system which provides for secretion of the product may be selected.

In particular, it appears that the mature TGF-β2, a disulfide-linked homodimer of 112 amino acids per subunit may be formed by cellular processing involving proteolytic cleavage between the Arg-Ala amino acids of the precursor (residue numbers 330 and 331 in FIG. 1B). In addition, the TGF-β2 precursor contains three potential N-glycoylation sites not found in the mature form; the proper glycosylation of the precursor may be important to the cellular synthesis and release or secretion of the mature molecule. In this regard, applicants have determined that the pro region of the TGF-β2 precursor is glycosylated and phosphorylated (see Section 10.2, infra). Moreover, the mature form of TGF-β2 comprises a disulfide-linked dimer involving nine cysteine residues per subunit. Some of these are involved in interchain and others in intrachain disulfide bonds which affect the tertiary structure and configuration of the mature molecule, and, as a result, its biological activity. Thus, the ability of a host cell used in the expression system to correctly express and process the TGF-β2 gene product is important to the production of a biologically active, mature TGF-β2 as well as to the production of TGF-β2 precursor forms.

A variety of animal host/expression vector systems (i.e., vectors which contain the necessary elements for directing the replication, transcription and translation of the TGF-β2 coding sequence in an appropriate host cell) may be utilized equally well by the skilled artisan. These include, but are not limited to, virus expression vector/mammalian host cell systems (e.g., cytomegalovirus, vaccinia virus, adenovirus, and the like); insect virus expression vector/insect cell systems (e.g., baculovirus); or nonviral promoter expression systems derived from the genomes of mammalian cells (e.g., the mouse metallothionein promotor).

The expression elements of these vectors vary in their strength and specificities. Depending on the host/vector system utilized, any one of a number of suitable transcription and translation elements may be used. For instance, when cloning in mammalian cell systems, promoters isolated from the genome of mammalian cells, (e.g., mouse metallothioneion promotor) or from viruses that grow in these cells, (e.g., vaccinia virus 7.5K promoter) may be used. Promoters produced by recombinant DNA or synthetic techniques may also be used to provide for transcription of the inserted sequences.

Specific initiation signals are also required for sufficient translation of inserted protein coding sequences. These signals include the ATG initiation codon and adjacent sequences. In cases where the entire TGF-β2 gene including its own initiation codon and adjacent sequences are inserted into the appropriate expression vectors, no additional translation control signals may be needed. However, in cases where only a portion of the coding sequence is inserted, exogenous translational control signals, including the ATG initiation codon, must be provided. Furthermore, the initiation codon must be in phase with the reading frame of the TGF-β2 coding sequences to ensure translation of the entire insert. These exogenous translational control signals and initiation codons can be a variety of origins, both natural and synthetic. The efficiency of expression may be enhanced by the inclusion of transcription attenuation sequences, enhancer elements, etc.

Any of the methods previously described for the insertion of DNA fragments into a vector may be used to construct expression vectors containing the TGF-β2 gene and appropriate transcriptional/translational control signals. These methods may include in vitro recombinant DNA techniques, synthetic techniques and in vivo recombinations (genetic recombination).

In cases where an adenovirus is used as an expression vector, in TGF-β2 coding sequences may be ligated to an adenovirus transcription/translation control complex, e.g., the late promoter and tripartitie leader sequence. This hybrid gene may then be inserted in the adenovirus genome by in vitro or in vivo recombination. Insertion in a non-essential region of the viral genome (e.g., region E1 or E3) will result in a recombinant virus that is viable and capable of expressing TGF-β2 in infected hosts. Similarly, the vaccinia 7.5K promoter may be used.

An alternative expression system which could be used to express TGF-β2 is an insect system. In one such system, Autographa californica nuclear polyhedrosis virus (AcNPV) is used as a vector to express foreign genes. The virus grows in Spodoptera frugiperda cells. The TGF-β2 coding sequence may be cloned into non-essential regions (for example the polyhedrin gene) of the virus and placed under control of an AcNPV promoter (for example the polyhedrin promoter). Successful insertion of the TGF-β2 coding sequence will result in inactivation of the polyhedrin gene and production of non-occluded recombinant virus (i.e., virus lacking the proteinaceous coat coded for by the polyhedrin gene). These recombinant viruses are then used to infect Spodoptera frugiperda cells in which the inserted gene is expressed.

In addition, a host cell strain may be chosen which modulates the expression of the inserted sequences, or modified and processes the gene product in the specific fashion desired. Expression from certain promoters can be elevated in the presence of certain inducers, (e.g., zinc and cadmium ions for metallothionein promoters). Therefore, expression of the genetically engineered TGF-β2 may be controlled. This is important if the protein product of the cloned foreign gene is lethal to host cells. Furthermore, modifications (e.g., glycosylation) and processing (e.g., cleavage) of protein products are important for the function of the protein. Different host cells have characteristic and specific mechanisms for the post-translational processing and modification of proteins. Appropriate cell lines or host systems can be chosen to ensure the correct modification and processing of the foreign protein expressed.

5.3. IDENTIFICATION OF TRANSFECTANTS OR TRANSFORMANTS EXPRESSING THE TGF-β2 GENE PRODUCT

The host cells which contain the recombinant TGF-β2 coding sequence and which express the biologically active, mature product may be identified by at least four general approaches: (a) DNA-DNA hybridization; (b) the presence or absence of "marker" gene functions; (c) assessing the level of transcription as measured by the expression of TGF-β2 mRNA transcripts in the host cell; and (d) detection of the mature and/or precursor gene products as measured by immunoassay and, ultimately, by its biological activity.

In the first approach, the presence of the TGF-β2 coding sequence inserted in the expression vector can be detected by DNA-DNA hybridization using probes comprising nucleotide sequences that are homologous to the TGF-β2 coding sequences substantially as shown in FIGS. 1A–1C, or portions or derivatives thereof.

In the second approach, the recombinant expression vector/host system can be identified and selected based upon the presence or absence of certain "marker" gene functions (e.g., thymidine kinase activity, resistance to antibiotics, resistance to methotrexate, transformation phenotype, occlusion body formation in faculovirus, etc.). For example, if the TGF-β2 coding sequence is inserted within a marker gene sequence of the vector, recombinants containing the TGF-β2 coding sequence can be identified by the absence of the marker gene function. Alternatively, a marker gene can be placed in tandem with the TGF-β2 sequence under the control of the same or different promoter used to control the expression of the TGF-β2 coding sequence. Expression of the marker in response to induction or selection indicates expression of the TGF-β2 coding sequence.

In the third approach, transcriptional activity for the TGF-β2 coding region can be assessed by hybridization assays. For example, polyadenylated RNA can be isolated and analyzed by Northern blot using a probe homologous to the TGF-β2 coding sequence or particular portions thereof. Alternatively, total nucleic acids and the host cell may be extracted and assayed for hybridization to such probes.

In the forth approach, the expression of the mature and/or precursor protein products can be assessed immunologically, for example by Western blots, immunoassays such as radioimmuno-precipitation, enzyme-linked immunoassays and the like. The ultimate test of the success of the expression system, however, involves the detection of the biologically active TGF-β2 gene product. Where the host cell secretes the gene product the cell free media obtained from the cultured transfectant host cell may be assayed for TGF-β2 activity. Where the gene product is not secreted, cell lysates may be assayed for such activity. In either case, biological assays such as the growth inhibition assay described herein or the stimulation of anchorage independent growth in target cells (Twardzik and Sherwin, 1985, J. Cell. Biochem. 28:289–297; Delarco and Todaro, 1978, Proc. Natl. Acad. Sci. U.S.A. 75:4001–4005) or the like may be used.

Once a clone that produces high levels of biologically active TGF-β2 is identified, the clone may be expanded and the TGF-β2 may be purified using techniques well known in the art. Such methods include immunoaffinity purification, chromatoraphic methods including high performances liquid chromatography, and the like.

5.4. STABLE EXPRESSION OF TGF-β2 IN CHO CELLS USING A HYBRID TGF-β1/β2 PRECURSOR GENE

In a particular embodiment of the invention, Chinese Hamster Ovary (CHO) cells transfected with a recombinant expression plasmid containing the coding sequence for a hybrid TGF-β1/(NH₂)/β2 (COOH) precursor, synthesized and secreted correctly processed, biactive, mature TGF-β2. The hybrid precursor protein encoded by the expression plasmid, termed TGF-β1(NH₂)/TGF-β2(COOH), was correctly processed in the transfected CHO cells as determined by immunoblotting, receptor binding and amino acid sequencing studies, described in detail in Section 8, infra.

The ability of the TGF-β1 amino-terminal precursor domain to direct the maturation of recombinant TGF-β2 raises questions concerning the molecular events involved with the processing of mature TGF-β2, and suggests that TGF-β1 and TGF-β2 may share a common maturation pathway. The suggestion that the amino-terminal domain of the TGF-β1 precursor plays an active role in the processing of mature TGF-β1 is supported by the discovery that this domain contains mannose-6-phosphate residues which enable the precursor to bind to mannose-6-phosphate receptors (Purchio et al., 1988, J. Biol. Chem. 263:14211–15215). The binding of TGF-β precursors to mannose-6-phosphate receptors likely acts to direct the molecule to lysosomes where processing can occur with the aid of lysosomal proteases. The presence of mannose-6-phosphate residues in the amino-terminal domain of the TGF-β1 precursor implicate a functional role for this domain of the precursor in the maturation of TGF-β1. Applicants' discovery that a hybrid TGF-β precursor which includes this domain is correctly processed to form mature TGF-β2 suggests the existence of a maturation pathway commonly followed by both TGF-β1 and TGF-β2. Nevertheless, it appears that the effectiveness and efficiency with which such a pathway executes processing events is variable and may depend on the overall structure composition of the precursor molecules following it. In this regard, COS cells transfected with a plasmid encoding the full TGF-β2 precursor protein appear to be considerably more efficient in processing mature growth factor compared to COS cells transfected with plasmids encoding either the full TGF-β1 or hybrid TGF-β1(NH₂)/TGF-β2(COOH) precursor proteins (Section 9, infra). Although the reasons for this observed processing variability are presently unknown, recognition of cleavage sites by proteases may be among the factors involved. For example, protease recognition and action may favor a particular secondary structure over others, thus, one precursor form may be a better substrate for processing than another.

The present invention also relates to purified recombinant TGF-β2. Bioactive TGF-β2 may be purified from the serum-free conditioned media of cultured CHO transfectants. Details of such purification methods are given in Sections 8 and 10, infra. The purified recombinant TGF-β2 of the invention migrates as a single 12 kD protein under reducing conditions and a single 24 kD protein under non-reducing conditions when analyzed by SDS-polyacrylamide gel electrophoresis, indicating the homogeneity of the preparation. Sequence analysis reveals that the recombinant product is correctly processed and has the same amino-terminal amino acid sequence as natural TGF-β2. Receptor binding studies show that the recombinant TGF-β2(rTGF-β2) binds to TGF-β receptors on human embryonic palatal mesenchyme (HEPM) cells. In summary, the purified rTGF-β2 of the invention appears to be immunologically, functionally and structurally identical to natural TGF-β2.

5.5. TRANSIENT EXPRESSION OF TGF-β2 IN COS CELLS

In another embodiment of the invention, bioactive mature TGF-β2 is produced by African green monkey COS cells transfected with expression plasmids containing either the coding sequence for the hybrid precursor discussed above or the coding sequence for the entire TGF-β2 precursor. For analytical comparison purposes, COS cells are also transfected with constructs programming the synthesis of the entire TGF-β1 precursor. In all three cases, mature and precursor growth factor products are secreted by the transfected COS cells. In all cases, the mature protein are largely secreted in their biologically latent forms, results consistent with the secretion of biologically latent TGF-$\beta$1 in transfected CHO cells (Gentry et al., 1987, J. Mol. Biol. 7:3418-3427). Obtaining the maximum bioactive product requires a routine acidification step which activates the latent form.

COS transfectants expressing the coding sequence for the TGF-$\beta$2 precursor secrete considerably more biologically active protein than COS transfectants expressing the coding sequences for either TGF-$\beta$1 or the hybrid TGF-$\beta$1(NH$_2$)/$\beta$2(COOH) precursors. These observations, discussed in detail in Section 9, infra, indicate that fewer mature TGF-$\beta$2 monomer remain associated with high molecular weight precursor proteins in the cells expressing TGF-$\beta$2 precursor. Such disulfide-linked associations between monomeric TGF-$\beta$1 and TGF-$\beta$1 precursors have been observed (Gentry et al., 1977, Mol. Cell. Biol., in press) and may act as intermediate complexes in the processing scheme. One possible explanation for the increased biological activity secreted by cells transfected with the TGF-$\beta$2 precursor may be that the TGF-$\beta$2 is more efficiently recognized and cleaved by proteases than are the TGF-$\beta$1 and hybrid TGF-$\beta$1/$\beta$2 precursors. Alternatively, secondary structural characteristics of the TGF-$\beta$2 precursor may render it more amenable to processing than the other TGF-$\beta$ precursors. The proposition that increased levels of bioactive recombinant TGF-$\beta$2 are obtained by utilizing the complete TGF-$\beta$2 precursor gene is further supported by the experimental data obtained by applicants in connection with a particular embodiment of the invention, discussed in Sections 5.6. and 10., infra.

5.6. STABLE HIGH-LEVEL EXPRESSION OF TGF-$\beta$2 IN CHO CELLS USING A TGF-$\beta$2-414 PRECURSOR GENE In a particular embodiment of the invention, described in detail by way of example in Section 10., infra, high levels of rTGF-$\beta$2 are synthesized and secreted by CHO cells transfected with an expression plasmid containing the coding sequence for the 414 amino acid TGF-$\beta$2 precursor and subsequently amplified for expression with methotrexate ($\beta$2(414) cl.32 cells). The TGF-$\beta$2 is secreted in a latent form, as acidification is necessary for detection of maximal levels of biological activity.

Amino-terminal sequencing of purified rTGF-$\beta$2 indicates that the mature growth factor is proteolytically processed at the predicted cleavage site (Ala 303 in TGF-$\beta$2(414)). Furthermore, protein sequence analysis of the carboxy-terminal cyanogen bromide peptide of rTGF-$\beta$2 suggests an intact protein. Thus, CHO cells possess the appropriate protease(s) to correctly process pro-TGF-$\beta$2.

Analysis of recombinant proteins secreted by these CHO cell transfectant by immunoblotting with anti-peptide antibodies specific for pro- and mature-region sequences indicates that three major pro-region containing proteins are secreted having molecular weights of 130 kD, 105 kD and 85 kD when analyzed by SDS-PAGE under non-reducing conditions. Only the 130 kD and 105 kD proteins are detected by an antibody to residues 367-379 of TGF-$\beta$2, suggesting that these proteins contain both mature and pro-region specific sequences, while the 85 kD band probably represents dimeric pro-region protein. Mature TGF-$\beta$2 is also detected by these antibodies.

The high molecular weight pro-region-containing proteins secreted by $\beta$2(414)cl.32 differe from those secreted by $\beta$1cl.17 in that the $\beta$1cl.17 cells secrete a single 90-110 kD complex. This difference is most likely due to the disulfide bonding pattern in the pro-region of the molecules since CHO cells transfected with the hybrid TGF-$\beta$1/$\beta$2 expression vector (Section 8, infra) secrete predominantly the 90-110 kD complex seen in $\beta$1cl.17-conditioned supernatants. Disruption of the 90-110 kD species and appearance of an 85 kD pro-region dimer can be seen in supernatants conditioned by COS cells transfected with plasmids encoding a mutant TGF-$\beta$1 precursor in which a cysteine at position 33 was replaced by serine (Brunner et al., 1989, J. Biol. Chem. 264:13660-13664), further suggesting that the disulfide bonding pattern within the pro-region contributes significantly to the formation of these high molecular weight complexes.

Analysis of conditioned media from $\beta$1(414)cl.32 cells by immunoblotting after fractionation by SDS-PAGE under reducing conditions demonstrates that the 12 kD TGF-$\beta$2 monomer and a 30-42 kD protein, containing only pro-region sequences, are the major secreted proteins (Section 10, infra). In contrast, only minor amounts of uncleaved pro-TGF-$\beta$2 are found, an observation further confirmed by analysis of total [$^{35}$S]-methionine and [$^{35}$S]-cysteine, [$^{32}$P]-orthophosphate, and [$^{3}$H]-glucosamine labeled proteins secreted by these cells (Section 10., infra).

Previous experiments have indicated that rTGF-$\beta$1 precursor contains mannose-6-phosphate (M-6-P) at two of three glycosylation sites within the pro-region. The pro-region of the TGF-$\beta$2(414) precursor is also glycosylated and contains M-6-P (Section 10.2.3., infra). M-6-P is thought to serve as a recognition marker for binding to the M-6-P receptor which is involved in the transport of these proteins to acidic vesicles where further proteolytic processing can take place (Kornfeld, 1986, J. Clin. Invest. 77:1-6; Dahms et al., 1989, J. Biol. Chem. 264:12115-12118). The TGF-$\beta$1 precursor binds to the M-6-P receptor when the receptor is bound to plastic (Purchio et al., 1988, J. Biol. Chem. 263:14211-14215) or is overexpressed on the surface of CHO cells (Kovacina et al., 1989, Biochem. Biophys. Res. Comm. 160:393-403). Agents such as monensin, chloroquine and ammonium chloride, which block the action of acidic proteases, block cleavage of pro-TGF-$\beta$1 suggesting that binding to the M-6-P receptor and cleavage by acidic proteases might be involved in processing TGF-$\beta$1 precursor (Sha et al., 1989, Mol. Endocrinol. 3:1090-1098). It is possible that the same or a similar pathway is involved in processing the TGF-$\beta$2(414) precursor.

As noted above, rTGF-$\beta$2 is secreted by $\beta$2(414)cl.32 cells in a biologically latent form. This phenomenon has also been observed for mammalian cells secreting rTGF-$\beta$1 (Genry et al., 1987, Mol. Cell. Biol. 7:3418-3427; Madisen et al., 1989, DNA 8:205-212; Wakefield et al., 1989, Growth Factors 1:203-218), and may be due, at least in part, to a non-covalent association of mature rTGF-$\beta$1 with high molecular weight pro-region containing complexes.

6. EXAMPLE: cDNA CLONING OF TGF-β2 PRECURSOR FROM PC-3 CELLS

The following examples describe the cDNA cloning of TGF-β2 precursor coding sequences from the human prostatic adenocarcinoma cell line, PC-3, from which TGF-beta-2 was previously isolated.

6.1. MATERIALS AND METHODS

6.1.1. Growth of Cells and RNA Extraction

The human prostatic adenocarcinoma cell line, PC-3, was grown in tamoxifen-supplemented medium as described (Ikeda et al., 1987, Biochemistry 26:2406–2410). MCF-7 cells are grown in Dulbecco's modified Eagle's medium containing 10% fetal calf serum and 6 units/ml insulin. All other cell lines were grown in the same medium without insulin. Polyadenylated RNA was isolated by oligo[dT]-cellulose chromatography as described (Purchio and Fareed, 1979, J. Virol. 29:763–769).

6.1.2. cDNA Library Construction and Screening

Double-stranded cDNA was synthesized from polyadenylated RNA isolated from PC-3 cells treated with tamoxifen for 24 hours as described (Maniatis et al., 1982, in Molecular Cloning: A Laboratory Manual, Cold Spring Harbor Press, Cold Spring Harbor, N.Y.). cDNA fractions greater than 1000 base pairs were cloned into lambda gt10 as described (Webb et al., 1987, DNA 6:71–79). The library was first screened in duplicate with a [$^{32}$P]-labeled 24-fold degenerate probe complimentary to DNA encoding amino acids WKWIHEP (probe 1) which are conserved between TGF-β1 and TGF-β2:

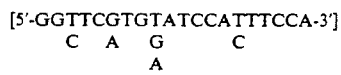

Positive clones were then screened with a second 128-fold degenerate probe complimentary to DNA encoding amino acids CFRNVQD (probe 2); five out of these seven amino acids are specific for TGF-Beta 2:

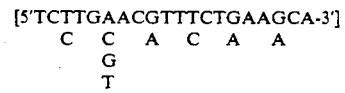

Hybridization was performed at 42° C. in 6XSSC, 5× Denhart's solution, 0.15 mM pyrophosphate, 100 micrograms/ml denatured calf thymus DNA, 100 micrograms/ml yeast tRNA and 1 mM EDTA (Maniatis et al., 1982, in Molecular Cloning: A Laboratory Manual, Cold Spring Harbor Press, Cold Spring Harbor, N.Y.). Filters were washed at 42° C. in 2XSSC, 0.1% NaDodSO$_4$, four times for 30 min. Several cDNA clones were isolated which hybridized to both probes and were subcloned into pEMBL (Dante et al., 1983, Nucleic Acids Res. 11:1645–1654). One clone (pPC-21) containing a 2.6 kb insert was sequenced on both strands by the dideoxy chain-termination method (Sanger et al., 1977, Proc. Natl. Acad. Sci. U.S.A. 74:5463–5467) using various restriction and exonuclease III deletion fragments combined with specific oligonucleotide priming (Henikoff, 1984, Gene 28:351–359). Another clone (pPC-14) containing a 2.2 kb insert was partially sequenced. Dot matrix analysis was performed on an IBM ATPC using Gene Pro software from Riverside Scientific Enterprises (Seattle, Wash.).

6.1.3. Northern Blot Analysis

Polyadenylated RNA was fractionated on a 1% agarose formaldehyde gel (Lehrach et al., 1977, Biochemistry 16:4743–4751), transferred to a nylon membrane (Hybond, Amersham), and hybridized to [$^{32}$P]-labeled probe. Hybridization was carried out at 42° C. in 50% formamide containing 0.9 M NaCl, 50 mM sodium phosphate (pH 7.0), 5 mM EDTA, 0.1% NaDodSO$_4$, 4× Denhardt's solution, 0.4 mg/ml of yeast tRNA, and 0.25 mg/ml of denatured calf thymus DNA. Filters were washed at.65° C. in 0.25× SSC. 0.1% NaDodSO$_4$, dried, and exposed to Cronex-4 X-ray film (DuPont) with the aid of Lightening Plus intensifier screens (DuPont).

6.2 RESULTS

A cDNA library was constructed using polyadenylated RNA isolated from tamoxifen treated PC-3 cells. Earlier observations indicated that tamoxifen treatment resulted in a 2- to 5-fold increase in the secretion of TGF-β2 (Ikeda et al., 1987, Biochemistry 26:2406:2410). The library was screened with probes 1 and 2 as described above. Five clones are obtained which hybridized to both probes: one clone, pPC-21, containing a 2.6 kb insert, was chosen for sequencing. Another clone, pPC-14, containing a 2.2 kb insert, was partially sequenced. The DNA and deduced amino acid sequences are shown in FIGS. 1A–1C.

pPC-21 contains a single open reading frame coding for a deduced polypeptide of 442 amino acids; the 112 carboxy terminal amino acids comprise the mature TGF-β2 monomer (boxed in FIGS. 1B–1C). The first methionine encoded by the open reading frame is immediately followed by a stretch of hydrophobic and uncharged amino acids (overlined in FIG. 1A) characteristic of a signal peptide. Neither the nucleotide sequence encoding this methionine nor those encoding the next two methionines present in the open reading frame are homologous to the consensus sequence for the intitiating methionine sequence (Kozak, 1986, Cell 44:283–292). Because translation usually initiates with the first methionine in an open reading frame and because regions homologous to TGF-β1, as discussed below, occur upstream of the second methionine, the first methionine has been tentatively assigned as the site of translation initiation. In appears then, that TGF-β2, like TGF-β1, is expressed as part of a much larger secreted precursor. The pPC-21 clone contains 467 bp upstream of the putative initiating methionine and a 3' untranslated region of approximately 800 bp including a poly [A] track, fifteen bases upstream of which is located a polyadenylation signal sequence (Proudfoot and Brownless, 1976, Nature 263:211–214).

The nucleotide sequence homology within the coding regions of the TGF-β1 and TGF-β2 pPC-21 cDNA clone was determined to be 53%. The regions encoding the mature proteins have 57% homology while the upstream precursor regions have 48% homology. After optimal alignment of the two sequences, several nucleotide insertions were noted in the TGF-β2 precursor region, one of which extended for 75 nucleotides. Whether these insertions are due to the presence of extra exons in TGF-β2 is unknown. No significant homology was detected between the DNA sequences in the non-coding regions of the two clones. In fact, while TGF-β1 has extended G-C rich non-coding regions, TGF-β2 has extensive A-T rich non-coding regions. Both cDNA clones contain repeating structural motifs in the 3' noncoding region with the repeats in TGF-β1 consisting of (purine) CCCC (Sharples et al., 1987, DNA 6:239-244) and in TGF-β2 of ATG or A(pryimidine) (purine).

Restriction mapping of many clones revealed that one clone, pPC-14, lacked a KpnI restriction site located in the amino portion of TGF-β2 coding sequence. Restriction maps of pPC-14 and pPC-21 are shown in FIG. 1H. pPC-14 was sequenced over a stretch of about 100 nucloetides corresponding to this region of the molecule by specifically priming with a 20-mer oligonucleotide complementary to nucleotides 277 to 296 in FIG. 1A. The results show that the pPC-14 clone contains an 87 nucleotide deletion (nucleotide positions 346 to 432 in FIG. 1A, see also FIG. 1I) that accounts for the missing KpnI site and which is replaced by the sequence AAT, the codon for Asparagine. The results suggest that the pPC-14 clone encodes a shorter TGF-β2 precursor for 414 amino acids differing from the sequence encoded by pPC-21 only in that amino acid residues 116 through 144 are deleted and replaced by a single Asparagine residue.

Although the entire coding region of pPC-14 was not determined, it is probably in perfect agreement with the pPC-21 coding sequence since, except for the KpnI site, restriction maps of the two clones overlap perfecting (FIG. 1H). Furthermore, a simian clone encoding a 414 amino acid TGF-β precursor containing the same 29 amino acid deletion and replacement has been identified, as described in Section 7, infra. This simian clone has a coding sequence which is nearly identical to that of the human pPC-21 clone in the regions 5' and 3' to the deletion.

Figure 2B:
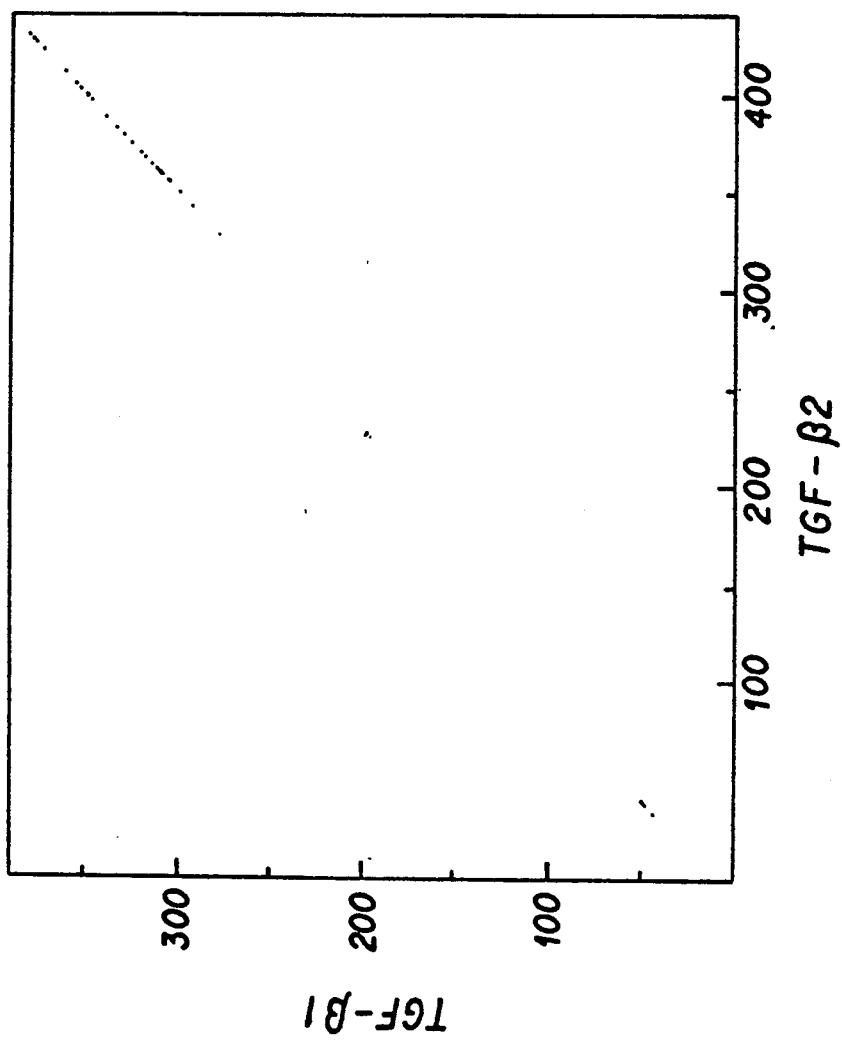
FIGS. 2B Dot matrix comparison using Gene Pro software. Each dot locates a point where 5 out of 10 amino acides are identical. Diagonal lines indicate regions of homology.

FIG. 2A shows the deduced protein sequence of human TGF-β1 (Derynck et al., 1985, Nature 316:701-705) compared to that of human TGF-β2-422. It was determined that TGF-β2 is 71% homologous with human TGF-β1 throughout the mature portion of the molecule as reported previously (Marquardt et al., 1987, J. Biol. Chem., 262:12127-12131). The amino portion of the precursor upstream of the mature molecule shows a 31% homology between TGF-β1 and TGF-β2-442. The dot matrix homology comparison shown in FIG. 2B reveals that significant homology exists in several specific areas of the proteins. Comparison of the N-terminal amino acid sequences in the putative signal peptide region reveals no significant homology.

In TGF-β2, the signal sequence cleavage site is predicted to be after amino acid 20 (serine) and after amino acid 29 (glycine) in TGF-β1 (Von Heijne, 1983, Eur. J. Biochem. 133:17-21). This cleavage site directly precedes the first block of homology between TGF-β1 and TGF-β2 which extends for 34 amino acids downstream. After removal of the signal sequences, the TGF-β1 and TGF-β2 precursors would share identical N-terminal over the first four amino acids, including the cysteine at position 4. Fourteen amino acids downstream of this putative N-terminus, 19 out of the next 21 amino acids are conserved between TGF-β1 and TGF-β2, a homology block larger than any seen even in the C-terminal region containing the mature protein. Several more blocks of strong homology, separated by long stretches of non homologous amino acids, exist within the region upstream of the mature protein as seen in FIGS. 2A and 2B.

The TGF-β2 precursor has three potential N-glycosylation sites (located at residues 72, 168, and 269 in FIGS. 1A-1B). Only the first site is conserved in TGF-β1, and lies within a larger block of conserved residues, suggesting that this potential glycosylation site has important structural and/or functional characteristics.

After removal of the signal sequence, the TGF-β2 precursor would contain either 31 or 59 amino acids more than its TGF-β1 counterpart. An additional cysteine residue in TGF-β2 is located just upstream of a large region of non-homologous amino acids that precedes the mature sequence. As with TGF-β1, the cleavage site of the mature TGF-β2 protein occurs just after a region of 4-5 basic amino acids as shown in FIG. 2A. The mature region contains nine cysteines. Conservation of 7 of the 9 cysteines is characteristic for the different members of the TGF-β family. Hydropathy analyses of TGF-β1 and TGF-β2 reveal similar patterns in both the precursor and mature regions with both proteins being generally hydrophilic in nature.

FIG. 3A shows a Northern blot analysis using pPC-21 to probe polyadenylated RNA from BSC-40 (an African green monkey kidney cell line) and tamoxifen-treated PC-3 cells. PC-3 cells contain three major TGF-β2-specific mRNA species of 4.1, 5.1 and 6.5 kb in size (FIG. 3A, lane 2); BSC-40 cells contain predominantly the 4.1 and 6.5 kb transcripts and lesser amounts of the 5.1 kb RNA (FIG. 3A, lane 1). Note that the pPC-21 probe does not detect the 2.5 kb TGF-β1-specific mRNA species present in this cell line under the hybridization conditions used here. These results and previous observations (Sharples et al., 1987, DNA 6:239-244) suggest that BSC-40 cells contain both TGF-β1- and TGF-β2-specific nRNA's. In order to demonstrate this more clearly, Northern blots were hybridized to a mixture containing equal amounts of TGF-β1 and TGF-β2 probes radiolabeled to the same specific activity. Lane 1 of FIG. 3B shows that BSC-40 cells contain the 2.5 kb TGF-β1-specific mRNA as well as the 4.1 and 6.5 kg TGF-β2 mRNA species: lane 2 of FIG. 3B shows that tamoxifen treated PC-3 cells also contain the 2.5 kb TGF-β1-specific mRNA. FIG. 3B also demonstrates that tamoxifen-treated PC-3 cells contain more TGF-β1-specific than TGF-β2-specific message.

Figure 4:
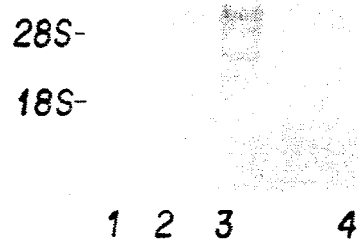
FIG. 4 Northern blot analysis of polyadenylated RNA from different sources. polyadenylated RNA was isolated from MCF-7 (human mammary carcinoma), SK-MEL 28 (human melonoma), KB (nasopharangeal carcinoma) and HBL-100 (human mammary epithelical) cells and analyzed by Northern blot hybridization to a TGF-β2 specific probe (pPC-21). Each lane contains 5 micrograms of polyadenylated RNA for SK-MEL 28 (lane 1), MCF-7 (lane 2), HBL-100 (lane 3) or KB (lane 4) cells.

The identification of TGF-β2-specific cDNA clones has enabled us to screen for TGF-β2 mRNA in various cell lines. The Northern blot shown in FIG. 4 shows that TGF-β2-specific transcripts could be detected in HBL100 (a normal epithelial cell line derived from human milk), MCF-7 (a human mammary carcinoma cell line), SK-MEL 28 (a melanoma cell line), and KB cells (a nasopharyneal carcinoma cell line) contain very low levels of TGF-β2 mRNA.

7. EXAMPLE: cDNA CLONING OF TGF-β2 PRECURSOR FROM BSC-40 CELLS

The following examples describe the cDNA cloning of TGF-β2 coding sequences from the African green monkey kidney cell line, BSC-40, shown to contain TGF-β2 specific mRNAs (Section 6, supra). The results indicate that simian TGF-β2, like human TGF-β2, is synthesized as one of at least two loner precursors from which the mature TGF-β2 molecule is derived by proteolytic cleavage.

7.1. MATERIALS AND METHODS

7.1.1. Growth of Cells and RNA Extraction

BSC-40 cells were grown in Dulbecco's modified Eagle medium containing 10% fetal calf serum. Polyadenylated RNA was isolated by oligo[dT]-cellulose chromatography as described (Purchio and Fareed, 1979, J. Virol. 29:763-769).

7.1.2. cDNA Library Construction and Screening

Double-stranded cDNA was synthesized from BSC-40 polyadenylated RNA as described (Maniatis et al., 1982, Molecular Cloning: A Laboratory Manual, Cold Spring Harbor Laboratory, Cold Spring Harbor, N.Y., 371-372) and, after treatment with EcoRI methylase, was ligated to oliogonucleotide linkers containing an EcoRI restriction enzyme recognition sites (EcoRI linkers). The cDNA was digested with EcoRI and fractionated by chromatography on Sephacryl S-1000. cDNA fractions of greater than 750 base pairs were pooled and ligated into lambda gt10 which had been cut with EcoRI (Davis et al., 1980, A Manual for Genetic Engineering: Advanced Bacterial Genetics; Cold Spring Harbor Laboratory, Cold Spring Harbor, N.Y.), packaged (Grosveld et al., 1981, Gene 13:227-237) and plated on $E$ $coli$ $C_{600}$ rK$^-$mK$^+$hfl. The library was screened by plaque hybridization (Bentonet et al., 1977, Science 196:180-182) to [$^{32}$P]-labeled pPC-21 and pPC-14 probes. Clone pBSC-40-16, which hybridized the pPC-21 probe, and clone pBSC-40-1, which hybridized the pPC-14 probe, were isolated and subcloned into pEMBL. The TGF-$\beta$2coding sequence of pBSC-40-1 was determined by sequencing both strands using the dideoxy chain-termination method (Sanger et al., 1977, Proc. Natl. Acad. Sci. U.S.A. 74:5463-5467). pBSC-40-16 was partially sequenced.

7.2. RESULTS

Two clones were obtained from a BSC-40 cDNA library which hybridized alternatively to provides constructed from the human TGF-$\beta$2-442 and TGF-$\beta$2-414 precursor coding sequences.

Clone pBSC-40-16, which hybridized to the TGF-$\beta$2-442 probe, was sequenced over a 150 nucleotides stretch (nucleotides 300 to 450 in FIG. 1A) expected to contain the coding sequence for the 29 amino acid segment, from positions 346 to 432 in FIG. 1a. The results show that, over this region, pBSC-40-16 encodes an amino acid sequence which is identical to the corresponding sequence in the human TGF-$\beta$2-442 cDNA clone, pPC-21, and suggest that pBSC-40-16 encodes a 442 amino acid TGF-$\beta$2 precursor.

Clone pBSC-40-1, which hybridized to the TGF-$\beta$2-414 probe, was sequenced over the entire coding region. The results indicate that this clone encodes a 414 amino acid TGF-$\beta$2 precursor which is identical to the human TGF-$\beta$2-442 precursor, except that amino acid residues 116 through 144 of human TGF-$\beta$2-442 are deleted and replaced by a single Asparagine residue. At the nucleotide level, pBSC-40-1 differs from human TGF-$\beta$2-442 in the deletion region: nucleotides 346 through 432 in FIG. 1a are deleted and replaced by the codon for Asparagine, AAT. Except for 13 silent base changes, the two structures are otherwise perfectly homologous over the remainder of the coding sequence.

8. EXAMPLE: EXPRESSION OF TGF-$\beta$2 IN CHO CELLS

The following examples describe the expression of mature, biologically active TGF-$\beta$2 in Chinese Hamster Ovary cells (CHO cells) transfected with a recombinant plasmid containing the coding sequence for mature human TGF-$\beta$2 ligated down-stress and in-frame with the coding sequence for the simian TGF-$\beta$1 precursor, under the regulatory control of the SV40 promoter sequences. The construct directed the synthesis and secretion of mature, biologically active TGF-$\beta$2 at a level of about 0.4 mg/L.

8.1. MATERIALS AND METHODS

8.1.1. Cell Culture

Dihydrofolate reductase (DHFR)-deficient Chinese Hamster Ovary (CHO) cells (Urlaub and Chasin, 1980 Proc. Natl. Acad. Sci. U.S.A. 77:4216) were propagated in Ham's F-12 medium (Gibco Laboratories, N.Y.) supplemented with 10% fetal bovine serum (FBS) and 150 ug/ml of L-proline. Penicillin and streptomycin were included at 100 U/ml and 100 ug/ml, respectively. CHO transfectants were grown in Dulbecco's modified Eagle's medium containing the same supplements as those designated above. CHO cells and their derivatives were routinely passaged by trypsinization at a 1:5 splitting ratio.

Methotrexate (Sigma, Mo.) was prepared at a stock concentration of 10 mg/ml in water, and was solubilized with the addition of dilute NaOH (0.2M) to a final pH of 6. The stock was filter-sterilized and stored at −20° C. Stock solutions of methotrexate in media (100 uM) were kept at 4° C. for no longer than 1 month.

8.1.2. DNA Manipulations and Plasmid Constructions

Restriction enzymes, T4 DNA ligase, calf intestinal phosphatase, the Klenow fragment of DNA polymerase I and other DNA reagents were purchased from Bethesda Research Laboratories, Md. Standard DNA manipulations were performed as outlined in Maniatis, T., et al., 1982, Molecular Cloning: A Laboratory Manual, Cold Spring Harbor Laboratory, N.Y.

Plasmid pSV2($\beta$1-TGF-dhfr), which contains the simian TGF-$\beta$1 cDNA and the mouse DHFR gene in tandem as well as intervening SV40 sequences, was constructed as described (Gentry et al., 1987, Mol. Cell. Biol. 7:3418).

Plasmid pSV2/$\beta$1-$\beta$2/dhfr was constructed as outlined in Section 8.2, infra.

8.1.3. DNA Transfections

Approximately 24 hours after seeding 10$^6$ DHFR-deficient CHO cells onto 100 mm dishes, the cultures were transfected with 20 ug of NdeI linearized pSV2-($\beta$1-TGF-dhfr) plasmid as a calcium phosphate precipitate (Wigler, M., et al., 1979, Proc. Natl. Acad. Sci. U.S.A. 76:1373-1376). Briefly, 20 ug of linearized DNA was added to 1 ml of 250 mM sterile CaCl$_2$. A 1 ml portion of 2× HEPES solution (280 mM NaCl, 50 mM HEPES, 1.5 mM sodium phosphate, pH 7.1) was then added dropwise, and the mixture was allowed to sit on ice for 30 minutes. The precipitate was then dispersed dropwise over the cells containing 10 ml of the F12 media. After incubation at 37° C. for 4 hours, the media was removed and replaced with 10 ml of F12 media containing 25% glycerol for 90 seconds at room temperature. Cells were rinsed once with 20 ml of F12 media and incubated in the nonselective F12 media (20 ml) for an additional 48 hours. Selection for DHFR-expressing transfectants was accomplished by replacing the media with DMEM supplemented with 10% dialyzed FBS (Gibco, N.Y.) and 150 ug/ml L-proline. Colonies were observed after culturing the cells 10-14 days in the selection media. Ten colonies were aspirated by a pasteur pipet and expanded.

8.1.4. Selection of Methotrexate Resistant Cells

Dihydrofolate reductase (DHFR)-amplified cells were derived from the primary transfectants essentially as described (Gasser, C. S. and Schimke, R. T., 1986, J. Biol. Chem. 261:6938-6946). After expansion, $10^5$ cells were seeded onto 100 mm dishes and adapted to increasing concentration of methotrexate. The plate containing visible colonies at the highest methotrexate concentration was trypsinized and adapted to that concentration of methotrexate for at least two additional 1:5 cell passages. Cells ($10^5$) were then seeded onto 100 mm dishes in 5 times the concentration of methotrexate. The dish containing visible colonies was again trypsinized and adapted in the methotrexate containing medium. Cells were frozen back at various stages of amplification in media containing 40% FBS, 10% dimethyl sulfoxide and 50% DMEM. Methotrexate was not included in the freezing media.

8.1.5. Growth Inhibition Assay

Mink lung epithelial cells, Mv 1 Lu (Accession Number CCL-64, American Type Culture Collection), which are extremely sensitive to TGF-$\beta$1, were utilized for the growth inhibition assay. The assay was performed using the thymidine analog 5'-[$^{125}$I]-iodo-2'deoxyuridine ($^{125}$idU) to assess DNA synthesis. One unit of activity was defined as the amount required to inhibit 50% incorporation of $^{125}$IdU compared to untreated CCL-64 cells.

To assay transfected cells for secretion of active TGF-$\beta$2, serum free supernatants were collected from one 24-hour collection on confluent cultures of cells and dialyzed extensively against 0.2M acetic acid. The acetic acid was removed by lypohilization and the sample was re-dissolved in sterile complete culture medium for assays.

8.1.6. Purification and Sequence Analysis of Recombinant Proteins

Serum and cell-free supernatants from 1$\beta$9, 12.5 CL36 cells were acidified to 1M acetic acid, concentrated, dialyzed against 0.2M acetic acid, lyophilized, and subjected to gel permeation chromatography on a Bio-Sil TSK-250 column using 0.1% TFA, 40% CH$_3$CN. The active fractions were pooled, diluted 1:1 with 0.05% TFA in H$_2$O and chromatographed on a $\mu$Bondapak C$_{18}$ column (3.9×300 mm) using 0.05% TFA and CH$_3$CN as the organic modifier. The active fractions were again pools, diluted 1:1 with 0.05% TFA in H$_2$O and rechromatographed on the same column using 0.05% TFA in H$_2$O and 1-propanol as the organic modifier (Ikeda et al., 1987, Biochemistry 26:2406-2410). Amino acid sequence analysis was performed on a model 470A amino acid sequencer (Applied Biosystems). Recombinant TGF-$\beta$1 (rTGF-$\beta$1) was purified form conditioned media of $\beta$-3-2000 cells as described (Gentry et al., 1988, Mol. Cell. Biol. 8:4162-4168).

8.1.7. Peptide Synthesis and Production of Antibodies

Peptides were synthesized by solid phase techniques on a Beckman 990 automated synthesizer and cleaved form the resin support as described (Gentry et al., 1987, Mol. Cell Biol. 7:3418-3427; Gentry and Lawton, 1986, Virology 152:421-431). Peptides were purified by high performance liquid chromatography and their amino acid compositions analytically confirmed.

Synthetic peptides were conjugated to bovine gamma-globulin as described (Gentry et al., 1987, Mol. Cell. Biol. 7:3418-3427; Gentry and Lawton, 1986, Virology 152:421-431). New Zealand white rabbits were primed at three to six sites by combined subcutaneous and intradermal inoculations with the peptide conjugates (100 $\mu$g equivalents of peptide) emulsified in Freunds complete adjuvant. Booster inoculations were administered at 2-3 week intervals. Rabbits were bled 7-14 days following the booster inoculations.

8.1.8. Immunoblotting

Proteins were fractionated on 7.5%-17.5% gradient SDS-polyacrylamide gels and transferred to unmodified nitrocellulose (0.45 um; Scheicher and Schuell) for 14-18 hours at 200 mA at 4° C. (Burnette, W. N., 1981, Anal. Biochem. 112:194-203). Excess binding capacity of the nitrocellulose was blocked by incubation with 2.5% BLOTTO (Johnson, D. A., et al., 1984, Gene Anal. Techn. 1:3-8) in phosphate-buffered saline (PBS) containing 0.2% NP-40. Rabbit anti-serum diluted 1:75 in 2.5% BLOTTO was incubated with the blocked nitrocellulose sheets for 2 hours at room temperature. After washing away excess antibody by five 5-minute washes in 2.5% BLOTTO, the nitrocellulose sheets were incubated with alkaline phosphatase-conjugated Protein A diluted 1:500 in 2.5% BLOTTO. Following a one hour incubation, the nitrocellulose sheets were washed 5 times in PBS (5 minute washes) containing 0.2% NP-40 and developed (Leary et al., 1983, Proc. Natl. Acad. Sci. U.S.A. 80:4045-4059).

8.1.9. Receptor Binding Assay rTGF-$\beta$2 and rTGF-$\beta$1 were labeled with [$^{125}$I] to a specific activity of 100-150 $\mu$Ci/$\mu$g by the chloramine T method as described (Frolik et al., 1984, J. Biol. Chem. 259:10995-11000). Confluent monolayers of human embryonic palatal mesenchymal (HEPM) cells, about 3×10$^5$ cells, were washed twice with binding buffer (DMEM plus 0.1% BSA and 25 mM Hepes buffer, pH 7.2) and incubated at 37° C. for 2 hours with the same buffer to dissociate any TGF-$\beta$ bound to cell surface receptors. The buffer was discarded and the monolayers were incubated with 1 $\mu$Ci of [$^{125}$I]-TGF-$\beta$1 or [$^{124}$I]-TGF-$\beta$2 at 4° C. for 3 hr in the presence or absence of 1000 ng/mL of the corresponding unlabeled protein. The monolayers were washed twice with ice-cold binding buffer and incubated for 15 minutes at 4° C. with 250 $\mu$M disuccinimidyl suberate. The monolayers were again washed three times with PBS and solubilized with 1% Triton X-100, 10 mM Tris, 1 mM EDTA pH 7.0. The soluble material was centrifuged at 12,000 x g prior to SDS-polyacrylamide gel analysis.

8.2. CONSTRUCTION OF TGF-BETA 1/TGF-BETA 2 HYBRID PRECURSOR GENE FOR TGF-$\beta$2 EXPRESSION A hybrid TGF-$\beta$ beta precursor gene consisting of simian TGF-$\beta$1 precursor coding and 5' untranslated sequences joined in-frame with human TGF-β2 mature coding and 3' untranslated sequences was constructed as illustrated in FIG. 1G.

pPC-21 was first digested with EcoRI, filled-in with Klenow enzyme, the 2.3 Kb fragment ligated into HincII digested pEMBL, and used to transform *E. coli*. Two clones, pPC-21/HincII+ and pPC-21/HincII−, having inserts in opposite orientations, were used to generate overlapping ExoIII digest fragments by digesting both with SstI and BamHI followed by ExoIII digestion, Klenow repair, religation of the DNA, and transformation of *E. coli*. Two clones, Exo 5.9 and Exo 25C were found to contain different lengths of 5' and 3' sequences, respectively and were subcloned into pEMBL to generate pEMBL 5.9 and pEMBL 25C.

pEMBL 5.9 was digested with HindIII, blunt ended with Klenow enzyme, digested with KpnI, and the 0.6 Kb fragment (fragment 1) was isolated. Exo 25C was digested with EcoRI and KpnI and the 1.1 Kb fragment (fragment 2) was isolated. pGS62 was digested with BamHI, filled in with Klenow enzyme, digested with EcoRI and ligated to fragments 1 and 2(pGS62 was derived from pGS20 (Mackett et al., 1984, J. Virol. 49:857) by deletion of a single EcoRI site). The mixture was used to transform *E. coli* and pGS62CIFB was isolated.

pGS62/CIFB was digested with PstI and EcoRI and the 1600 bp fragment was isolated and further digested with XhoII. The resulting 400 bp Xho-II-EcoRI fragment was isolated (fragment 3). pSV2-beta-TGF (Gentry et al., 1987, Mol. Cell. Biol. 7:3418) was digested with ApaI and EcoRI and the large 300 bp fragment was isolated (fragment 4).

Two complimentary strands of DNA with the sequences shown below were synthesized, phosphorylated, annealed and ligated to fragments '3' and '4' described above.

```
'5 CAA CAT CTG CAA AGC TCC CGG CAC CGC CGA GCT TTG
   GAT GCG GCC TAT TGC TTT AGA AAT GTG CAG GAT AAT
   TGC TGC CTA CGT CCA CTT TAC ATT GAT TTC AAG AGG 3'

5' GATC CCT CTT GAA ATC AAT GTA AAG TGG ACG TAG GCA
   GCA ATT ATC CTG CAC ATT TCT AAA GCA ATA GGC CGC
   ATC CAA AGC TCG GCG GTG CCG GGA GCT TTG CAG ATG
   TTG GGCC 3'
```

The ligation mixture was used to transform *E. coli* and plasmid pβ1/β2 was isolated.

Plasmid pβ1/β2 was digested with EcoRI, filled in with the Klenow fragment of DNA polymerase I, cut with HindIII and the 1600 bp fragment was isolated: pSV2, β1/β2 was constructed by inserting this fragment into pSV2, neo which had been previously digested with HindIII and HpaI to eliminate the neo gene.

pSV2,β1/β2 was digested with PvuI and EcoRI, filled in with Klenow enzyme, digested with NdeI and the 2.6 kb (approx.) NdeI-EcoRI fragment was isolated and ligated to pSV2, dhfr which had been digested with NdeI and PvuII. The ligation mixture was used to transform *E. coli* and pSV2/β1-β2dhfr was isolated.

8.3. EXPRESSION OF TGF-BETA 2 IN CHO CELLS pSV/β1-β2/dhfr was used to transfect DHFR-deficient CHO cells and DHFR-amplified cells were derived from the primary transfectants as described in Materials and Methods, supra. Positive clones were identified using the growth inhibition assay described in Section 8.1.5., supra. Recombinant proteins were also detected by Western blotting using an anti-peptide antisera made against the sequence $NH_2$-YNTIN-PEASASPC-COOH (Gentry et al., 1987, Mol. Cell, Biol. 7:3418) which is present in mature TGF-β2. Detection of optimal bioactivity required an acidification step prior to analysis.

Figure 5:
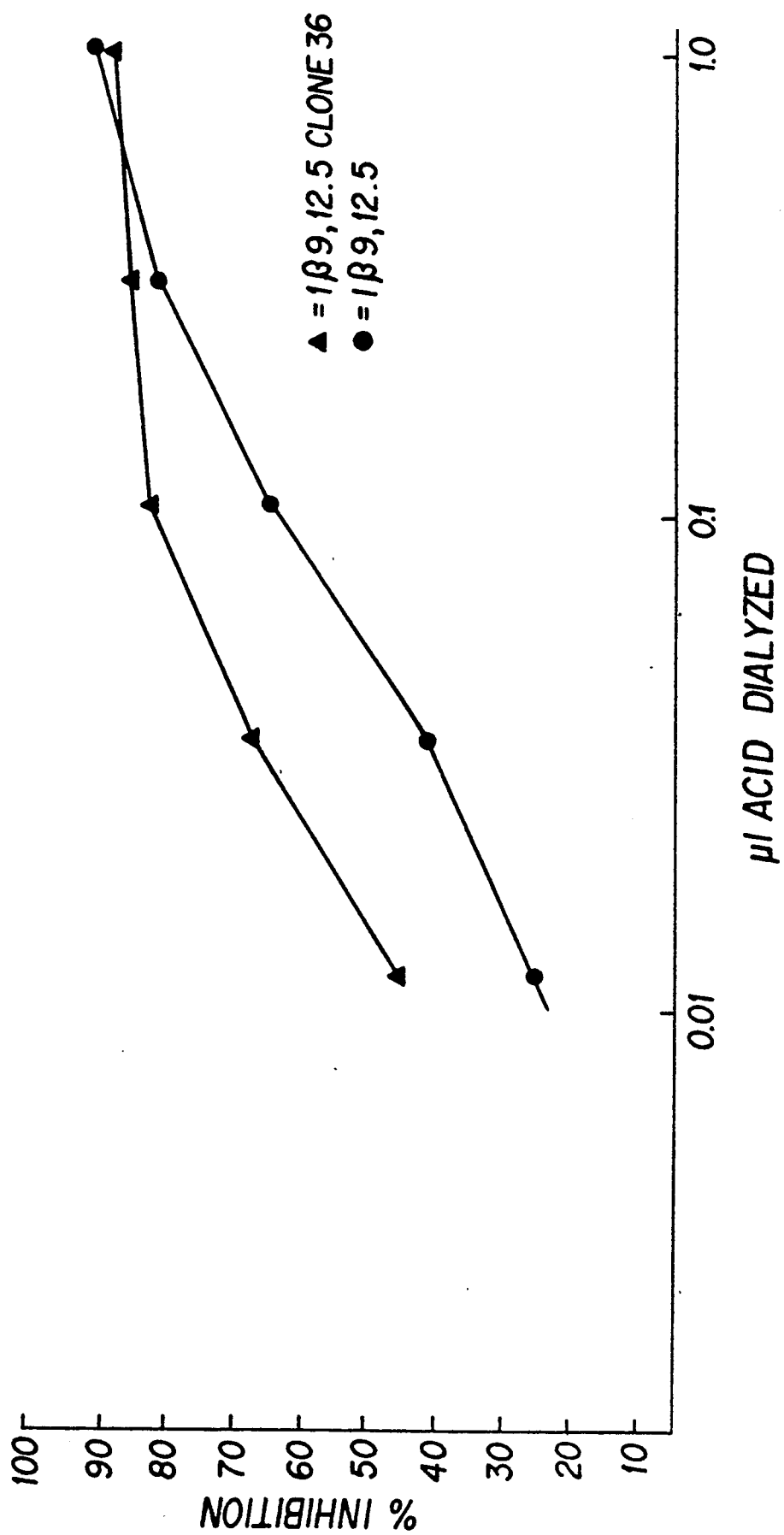
FIG. 5 Bioactivity Assay of Recombinant TGF-β2. 1B9, 12.5, clone 36 cells were grown to confluency in 100 mm tissue culture dishes. Cells were washed 3× with serum-free media and incubated for 24 hours in 5 ml of serum-free media. Media was collected, dialyzed against 0.2 M acetic acid, and assayed for inhibition of DNA synthesis in CCL64 cells as described (Gentry et al., 1987, Mol. Cell. Biol. 7.3418). In this assay 3.3 pg of TGF-β1 standard gave 50% inhibition; the specific activity of TGF-β2 was calculated to be about half that of TGF-β1.

One line, 1β9, 12.5, was found to secrete 240 ng/ml TGF-β2 (FIG. 5). This line was then cloned by limiting dilution in 96 well plates. One clone, 1β9, 12.5, CL36, produced approximately 400 ng/ml (FIG. 5) and was selected for further characterization.

Figure 6:
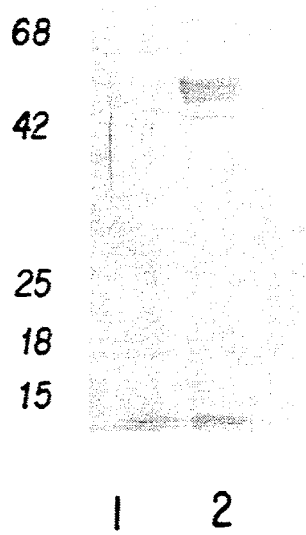
FIG. 6 Western blot analysis of recombinant proteins secreted by 1β9, 12.5, clone 36 cells. Acid dialyzed serum-free conditioned media from 1β9, 12.5, clone 36 cells was fractionated by SDS-polyacrylamide gel electrophoresis and analyzed by Western blotting with antiserum made against the synthetic peptide NH$_2$-YNTIN-PEASASPC-COOH (anti-TGF-β2 395-407) located at amino acid sequence 395-407 within the TGF-β2 precursor.

Analysis of the protein secreted by clone 1β9, 12.5, CL36 by Western blotting using anti-peptide antiserum is shown in FIG. 6, revealing the presence of the mature 24 kd TGF-β2 dimer as well as the larger (approx. 90 kd) precursor form.

8.4. ANALYSIS OF RECOMBINANT PROTEINS SECRETED BY TRANSFECTED CHO CELLS

The TGF-β1 precursor proteins produced by CHO cells are glycosylated, phosphorylated on mannose residues to yield mannose-6-phosphate, and bind to the mannose-6-phosphate receptor (Brunner et al., 1988, Mol. Cell. Biol, 8:2229–2232; Purchio et al., 1988, J. Biol. Chem. 263:14211–14215). Binding to the mannose-6-phosphate receptor has been implicated in the transport of intracellular proteins to lysosomes (for review see Kornfeld, 1986, J. Clin. Invest. 77:1–6), suggesting that the amino terminal precursor region of TGF-β1 may play a role in the proteolytic processing necessary to generate mature TGF-β1. It was of interest to further investigate the hybrid TGF-β1($NH_2$)/β2(COOH) to determine whether the amino-terminal precursor region of TGF-β1 could lead to correct processing of a functional mature TGF-β2 molecule. CHO cells were transfected with pSV2/β1-β/dhfr and individual clones amplified as described in Section 8.1., supra.

Immunoblot analysis of proteins secreted by 1β9, 12.5 clone 36 with anti-TGF-β2 $_{395-407}$ is shown in FIG. 7A; a 12 kD protein representing reduced TGF-β2 monomer as well as larger 45–55 kD precursor polypeptides can be seen (FIG. 7A, lane 2). Immunoblot analyses under non-reducing conditions revealed the 24 kD dimer as well as high molecular weight precursor species (FIG. 7B, lane 2). The immunoreactivity was blocked by preincubation of antisera with peptide (FIG. 7A, lane 3). The 12 kD and 24 kD rTGF-β2 proteins comigrated with reduced and non-reduced natural TGF-β2 (FIG. 7A, lane 1 and FIG. 7B, lane 1).

rTGF-β2 was purified from serum-free conditioned media as described in Section 8.1.6., supra. Analysis of rTGF-β2 by SDS-polyacrylamide gel electrophoresis followed by silver staining or immunoblotting is shown in FIG. 8A and FIG. 8B. Additional analysis following [$^{125}$I]-labeling is shown in FIG. 8C. The results demonstrate that CHO cells transfected and amplified with pSV2/β1-β/dhfr secrete a polypeptide having a molecular weight of 24 kD when analyzed under non-reducing conditions (12 kD under reducing conditions) which is immunologically and functionally equivalent to natural TGF-$\beta2$. Protein sequence analysis of the first twelve residues of the 24 kD protein shown in FIG. 8A demonstrated that it was identical to natural TGF-$\beta2$, thus indicating that mature TGF-$\beta2$ is correctly processed from the TGF-$\beta1$(NH$_2$)/$\beta2$(COOH) precursor.

Figure 9:
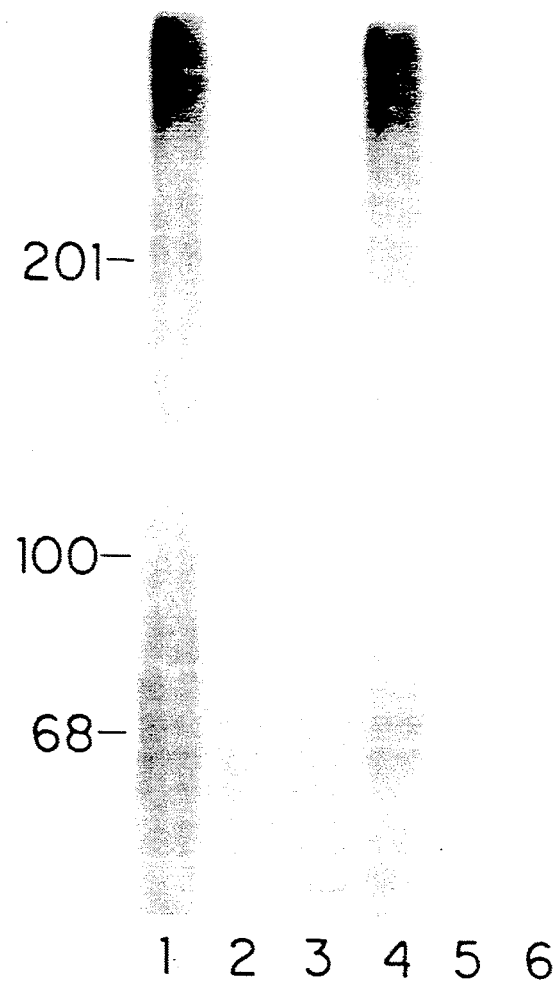
FIG. 9 Binding of rTGF-β2 to HEPM cell surface TGF-β receptros. TGF-β receptros affinity labeled with [$^{125}$I]-rTGF-β1 and [$^{125}$I]-rTGF-β2 were analyzed on a 6.25% polyacrylamide-SDS gel under reducing conditions. Lanes 1-3 were labeled with [$^{125}$I]-rTGF-β1 and competed with unlabeled rTGF-β1 (lane 2) or unlabeled rTGF-β2 (lane 3). Lanes 4-6 were labeled with [$^{125}$I]-rTGF-β2 and competed with unlabeled rTGF-β1 (lane 5) or unlabeled rTGF-β2 (lane 6).

Purified rTGF-$\beta2$ was further analyzed for its ability to bind cell surface receptors the TGF-$\beta$. The receptor binding assay was performed with HEPM cells as described in Section 8.1.9., supra, and the results are presented in FIG. 9. HEPM cell surface receptors for TGF-$\beta$ affinity labeled with [$^{125}$I]-rTGF-$\beta2$ and analyzed under reducing conditions on SDS-PAGE migrated into three distinct bands with the large majority of the signal localized in the high molecular weight band seen in FIG. 9, which likely corresponds to a type III TGF-$\beta$ receptor having a molecular weight of about 250 to 350 kD. Minor receptor binding components of about 90 kD and 65 kD were also detected (FIG. 9). Unlabeled rTGF-$\beta2$ was able to compete away the binding of [$^{125}$I]-rTGF-$\beta2$.

9. EXAMPLE: EXPRESSION OF TGF-$\beta2$ IN COS CELLS

The following examples describe the expression of mature bioactive and precursor forms of TGF-$\beta2$ in COS cells transfected with recombinant plasmids containing the coding sequence for TGF-$\beta2$ precursor, or TGF-$\beta1$/TGF-$\beta2$ hybrid precursor, under the regulatory control of cytomegalovirus and HIV expression regulatory elements. Two plasmids, one encoding the TGF-$\beta2$ precursor and one encoding the hybrid TGF-$\beta1$/TGF-$\beta2$ precursor, directed the synthesis and secretion of precursor and bioactive mature TGF-$\beta2$ polypeptides.

9.1. MATERIALS AND METHODS

9.1.1. Cell Culture

COS cells, an African green monkey kidney cell line, were propagated in DMEM media supplemented with 10% fetal calf serum. (Penicillin and streptomycin were included at 100 u/ml and 100 $\mu$g/ml, respectively). COS transfectants were grown in the same media. Cells were routinely passaged by trypsinization at a 1.5 splitting ratio.

9.1.2. Plasmid Constructions and COS Cell Transfections

Plasmids pTGF-$\beta2$, encoding simian TGF-$\beta1$ and pPC-21 (2.3 kb) (coding for human TGF-$\beta2$) have been described (Sharples et al., 1987, DNA 6:239–244; Madisen et al., 1988, DNA 7:1-8). The insert from $\lambda$BSC-1$\beta2$ (Webb et al., 1988, DNA 7:493–497) was subcloned into the EcoRI site of pEMBL to give pBSC40, 1/$\beta2$ (414) which contains sequences encoding simian TGF-$\beta2$. A synthetic double stranded DNA fragment comprising 92 nucleotides of 5'-untranslated sequence and the initial 73 nucleotides of the coding region of TGF-$\beta2$, up to the Pst I site (Webb et al., 1988, DNA 7:493–497; Hanks et al., 1988, Proc. Natl. Acad. Sci. U.S.A. 85:79-82) was prepared on an Applied Biosystems DNA synthesizer. This fragment was synthesized with a HindIII site at its 5'-end to facilitate ligation.

Plasmid pBSC40,1/$\beta2$(414) was digested with PstI and StyI to obtain the remainder of the TGF-$\beta2$ precursor coding and 3'-untranslated regions. Plasmid p$\pi$H3M (Aruffo and Seed, 1987, Proc. Natl. Acad. Sci. U.S.A. 84:8573-8577), lacking the polyliner between the XhoI sites, was digested with XhoI, filled-in with Klenow fragment, digested with HindIII and ligated to the two fragments described above to yield p$\beta2'$, encoding the TGF-$\beta2$ precursor.

Figure 10A:
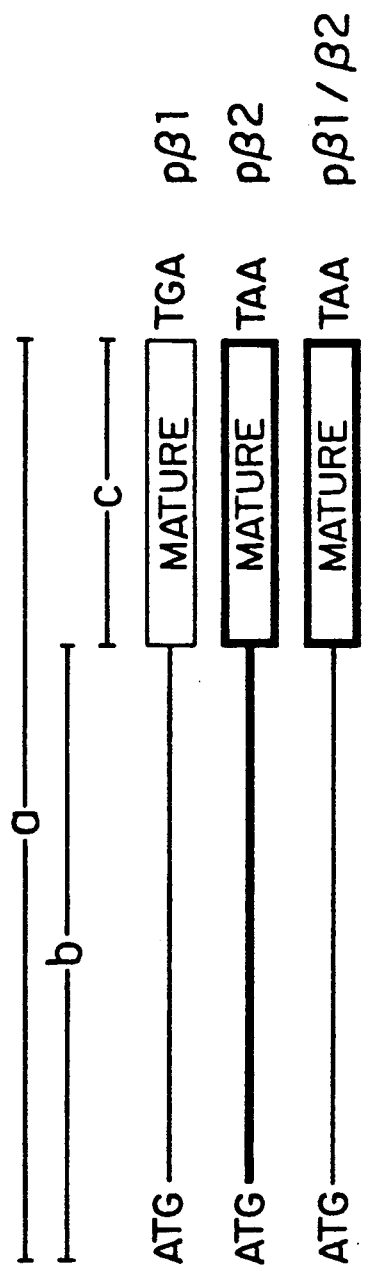
FIG. 10A: line diagrams of regions encoded by TGF-β plasmids. pβ1' encodes TGF-β1; pβ2' encodes TGF-β2; pβ1/β2' encodes the β1(NH$_2$)/β2(COOH) hybrid protein.

For expression in COS cells, the coding sequences for TGF-$\beta1$ and the hybrid TGF-$\beta1$(NH$_2$)/$\beta2$(COOH) were inserted into the same p$\pi$H3M vector as described above to create p$\beta1'$ and p$\beta1$/$\beta2'$. The TGF-$\beta$ coding regions contained within p$\beta1'$, p$\beta2'$, and p$\beta1$/$\beta2'$ are illustrated in FIG. 10A. DNA ligation, transformation of MC1061/p3 cells, and COS cell transfections were conducted as described (Seed and Aruffo, 1987, Proc. Natl. Acad. Sci. U.S.A. 84:8573-8577) with the following modifications: Transfections were performed in 100 mm dishes with 10$^6$ cells using 5 mL transfection material for 2.5 hours at 37° C. After a 48-hour incubation in DMEM+10% FBS, the media was replaced with serum-free DMEM. Transfected cells were incubated an additional 48 hours prior to harvesting conditioned media.

9.1.3. Analysis of Recombinant Proteins

Serum and cell-free conditioned media was collected from transfected cells, dialyzed against 0.2M acetic acid and assayed for growth inhibition of mink lung cells as described in Section 8.1.5, supra. Recombinant proteins were also analyzed by immunoblotting as described in Section 8.1.8., supra, using antisera to mature TGF-$\beta2$ peptide sequence 395–407 (anti-TGF-$\beta2_{395-407}$) located within the mature TGF-$\beta2$ region. The anti-TGF-$\beta2_{395-407}$ antisera was specific for TGF-$\beta2$ and did not cross react with TGF-$\beta1$ (FIG. 10C, lane 1); all reactivity of anti-TGF-$\beta2_{395-407}$ could be blocked by excess peptide (FIG. 7A, lane 3).

9.2. RESULTS

Transfection of COS cells with plasmids containing cDNAs encoding TGF-$\beta1$, TGF-$\beta2$, and TGF-$\beta1$(NH$_2$)/TGF-$\beta2$ (COOH) proteins resulted in the secretion of latent mature forms of TGF-$\beta1$ and TGF-$\beta2$. Detection of biological activity required prior acidification to activate the latent forms secreted by the transfected COS cells, results which are consistent with those obtained with transfected CHO cells secreting rTGF-$\beta1$ (Gentry et al., 1987, Mo.. Cell Biol. 7:3418-3427) and which suggest that secretion at latent mature TGF-$\beta2$ associated with precursor molecules is not a peculiarity of expression by CHO cells.

Line diagrams of the TGF-$\beta$ protein regions contained in p$\beta1'$, p$\beta2'$, and p$\beta1$/$\beta2'$ are shown in FIG. 10A. COS cells were separately transfected with each plasmid and serum-free supernatants were analyzed by immunoblotting. FIG. 10B shows that cells transfected with p$\beta1'$ secreted mature 12 kD TGF-$\beta1$ monomer (band c in FIG. 10A) as well as a 45–55 kD precursor species (band a in FIG. 10A) when analysed by immunoblotting under reducing conditions using anti-TGF-$\beta1_{369-381}$. These proteins are similar to those produced in CHO cells transfected with a plasmid expressing TGF-$\beta1$ cDNA (Gentry et al., 1987, Mol. Cell. Biol. 7:3418-3427). Note that band b, which does not contain mature TGF-$\beta1$, is not detected by this antisera.

COS cells transfected with p$\beta1$/$\beta2'$ secrete mature 12 kD TGF-$\beta2$ monomer and a higher molecular weight 45–55 kD species, both of which are detected by anti-TGF-$\beta2_{395-407}$ (FIG. 10C, lane 2). Analysis under non-reducing conditions revealed the 24 kD TGF-$\beta$2 dimer secreted by these cells, as well as high molecular weight precursor proteins (FIG. 10D). The anti-TGF-$\beta2_{395-407}$ antisera appears to be specific for TGF-$\beta$2 as no cross-reactivity with rTGF-$\beta$1 proteins was detected (see FIG. 10C, lane 1). COS cells transfected with p$\beta$2' also secreted a 12 kD TGF-$\beta$2 monomer as well as a 50 kD precursor protein (FIG. 10E, lane 1) when analyzed under reducing conditions. Note that cells transfected with p$\beta$1/$\beta$2' (FIG. 10E, lane 2) produced considerably more high molecular weight precursor protein than cells transfected with p$\beta$2' (FIG. 10E, lane 1).

Table I shows that biologically active TGF-$\beta$1 and TGF-$\beta$2 is secreted by the transfected COS cells; detection of maximal growth inhibitory activity required an acidification step prior to analysis.

TABLE I

GROWTH INHIBITORY BIOACTIVITY OF MEDIA CONDITIONED BY TRANSFECTED COS CELLS

| | Activity; pg/$\mu$L[1] | |
|---|---|---|
| | + Acid | − Acid |
| p$\beta$1' | 11.8 | 0.3 |
| p$\beta$2' | 93.0 | 0.9 |
| p$\beta$1/$\beta$2' | 8.3 | <0.1 |

[1]COS cells were transfected with p$\beta$1', p$\beta$2' and p$\beta$1/$\beta$2'; 48 hrs post-transfection, supernatants were replaced with serum-free media; 48 hrs later, conditioned media was collected, dialyzed against 0.2M acetic acid (+ acid) or 50 mM NH$_4$HCO$_3$, pH 7.4 (− acid) and assayed for growth inhibitory activity on CCL64 cells as described in Section 8.1.5, supra.

10. EXAMPLE: HIGH-LEVEL EXPRESSION OF SIMIAN TGF-$\beta$2 AND THE 414 AMINO ACID SIMIAN TGF-$\beta$2 PRECURSOR IN CHINESE HAMSTER OVARY CELLS Described here is the high level expression of mature TGF-$\beta$2 and the 414 amino acid TGF-$\beta$2 precursor in Chinese Hamster Ovary cells transfected with a recombinant plasmid encoding simian TGF-$\beta$2(414) precursor and dihydrofolate reductase (DHFR) under the regulatory control of the SV-40 promotor. Amplification of expression with methotrexate resulted in the isolation of clones secreting high levels of mature TGF-$\beta$2 as well as high-molecular weight precursor complexes. Preliminary characterization of the secreted TGF-$\beta$2 precursor indicated that its pro-region is glycosylated and contains mannose-6-phosphate.

10.1. MATERIALS AND METHODS

10.1.1. Cell Culture

Dihydrofolate reductase (DHFR)-deficient Chinese Hamster Ovary (CHO) cells were propagated as described in Section 8.1.1., supra.

10.1.2. DNA Manipulations and Plasmid Constructions

Standard DNA manipulations were performed as outlined in Maniattis et al., 1982, Molecular Cloning: A Laboratory Manual, Cold Springs Harbor Laboratory, New York.

pTGF-$\beta$2(414), an expression plasmid encoding simian TGF-$\beta$2-414 and DHFR was constructed as follows: pBSC-40-1 (Section 7.2., supra) encoding simian TGF-$\beta$2-414 was used to construct a second TGF-$\beta$2 gene in pEMBL which begins at the PstI site of the coding sequence, 74 base pairs downstream of the translation start site, and terminates at the StyI site 100 base pairs past the translation stop codon TAA. pBSC-40-1 was digested with StyI, repaired to blunt ends with the Klenow enzyme of DNA polymerase I, and digested with SphI. The resulting 298 bp fragment having SphI-StyI (blunt) ends was isolated. pBSC-40-1 was also digested with PstI and SphI and the 976 bp fragment was isolated. These two fragments were ligated into pEMBL which had previously been digested with PstI and SmaI to yield p$\beta$2 (Pst-Sty).

The TGF-$\beta$2 coding sequence within p$\beta$2 (Pst-Sty) was then isolated as one fragment by digesting p$\beta$2 with Eco RI, treating with Klenow enzyme, and digesting with PstI. This 1.3 Kb fragment, still missing the first 73 TGF-$\beta$2 encoding nucleotides, was ligated into pSV2-neo, which had previously been digested with HindIII and HpaI (to eliminate the neo gene) along with a synthetic double stranded DNA fragment comprising 92 nucleotides of 5' untranslated sequence and the initial 73 nucleotides (up to the PstI site) of the TGF-$\beta$2 coding sequence (Section 9.1.2., supra; Madisen et al., 1989, DNA 8:205–212). The resulting ligation product was used to construct the expression vector pTGF-$\beta$2(414), a pSV2 expression vector containing genes encoding TGF-$\beta$2-4141 and DHFR.

10.1.3. DNA Transfections and Selection of Methotrexate Resistant Cells pTGF-$\beta$2 was transfected into CHO cells and amplified clones were obtained essentially as described (Gentry et al., 1987, Mol. Cell. Biol. 7:3418–3427), with minor modifications. After transfection, cells expressing DHFR were selected by replacing the non-selective F-12 media with DMEM containing 10% FBS and 150 ng/ml L-proline and 0.3 mg/ml glutamine. Colonies were picked, expanded, and 10$^5$ cells were seeded onto a 100 mm tissue culture dish and adapted to 0.1 $\mu$M methotrexate. Plates were trypsinized and cells were carried for three passages at 1:5 split ratios. At that time, 10$^5$ cells were successively adapted to 0.5, 2.5, 10.0 and 50.0 $\mu$M methotrexate. Cell lines were cloned by limiting dilution in 96-well dishes. Two clones, $\beta$2(414)c1.32 and $\beta$2(414)c1.35, growing at 10 $\mu$M and 50 $\mu$M methotrexate, respectively, were isolated. Both clones secrete approximately 5 $\mu$M/ml TGF-$\beta$2 and were chosen for further characterization. A clone of CHO cells secreting rTGF-$\beta$1, hereinafter referred to as $\beta$1c1.17, was isolated and propagated in 20 $\mu$M methotrexate as described (Purchio et al., 1988, J. Biol. Chem. 263:14211–14215).

10.1.4. Northern Blot Analysis

Total cellular RNA was fractionated on 1% agarose-formaldehyde gel (Lehrach et al., 1977, Biochemistry 16:4743–4751), transferred to a nylon membrane (Hybond, Amersham) and hybridized to [$^{32}$P]-labeled probe (pPC-21(2.3 kb)), as described in Section 6.1.3., supra.

10.1.5. Analysis of Secreted Proteins by Page and Two Dimensional Electrophoresis Serum- and cell-free conditioned media were labeled with [$^{35}$S]-cysteine plus [$^{35}$S]-methionine, [$^3$H]-glucosamine, and [$^{32}$P]-orthophosphate as described (Brunner et al., 1988, Mol. Cell. Biol. 8:2229–2232) and analyzed by PAGE on either 15% or 7.5–17.5% polyacrylamide gels under reducing or non-reducing conditions. Gels containing [$^{35}$S] and [$^3$H] were fluorographed before exposure to Cronex-4 X-ray film. Two-dimensional electrophoresis of acid hydrolysates of [$^{32}$P]-labeled proteins was performed as described (Cooper et al., 1983, Methods Enzymol. 99:387–402).

10.1.6. Immunoblot Analysis and Anti-Peptide Antibodies

Anti-peptide antiserum generated against the TGF-β2-414 peptide sequence 367-379 (anti-TGF-β2(414)-367-379, FIG. 12A), located within the mature TGF-β2 region, was obtained as described in Section 8.1.7., supra. This antiserum has been previously characterized and shown to be specific for TGF-β2: it did not react with TGF-β1 and all reactivity was blocked by incubation with excess unlabeled peptide (Section 9, supra; note that this antisera is termed anti-TGF-β2$_{395-407}$ in Section 9 to correspond to the residue numbering for the 442 amino acid TGF-β2 precursor). Anti-peptide antiserum against the peptide sequence corresponding to amino acids 51-66 (anti-TGF-β2(414)$_{51-66}$, FIG. 12A), located within the pro-region of TGF-β2(414), was produced as described in Section 8.1.7., supra. Anti-TGF-β1$_{81-94}$ and anti-TGF-β1$_{369-381}$, anti-peptide antisera directed against the pro-and mature-regions of TGF-β1 precursor, have been described (Gentry el al., 1987, Mol. Cell. Biol. 7:3418-3427). Confluent cells were washed 3× in serum-free medium and incubated in serum-free medium for 24 hours; serum- and cell-free conditioned media were dialyzed against 0.2M acetic acid and analyzed by immunoblotting as described in Section 8.1.8., supra.

10.1.7. Growth Inhibition Assay

Cells were grown to confluency on 100 mm dishes and washed 3× with serum-free medium; 5 ml of serum-free medium was then added and cells were incubated for 24 hours. The media was collected dialyzed against 0.2M acetic acid or 50 mM NH$_4$HCO$_3$, pH 7.0, and assayed for growth inhibition of mink lung cells as described in Section 8.1.5, supra. In this assay, TGF-β1 and TGF-β2 have similar specific activities.

10.1.8. Purification and Sequence Analysis of Recombinant Proteins

Serum- and cell-free conditioned media from β2(414)c1.32 cells was acidified with acetic acid (56 ml glacial acetic acid per liter of media) and then dialyzed against 0.2M acetic acid. The solution was then adjusted to pH 4.0 with 1N NaOH and clarified by centrifugation at 25,000 xg. The supernatant was applied to a column (1×12 cm) packed with CM-Trisacryl previously equilibrated with 50 mM sodium acetic pH 4.0. Elution of rTGF-β2 was achieved using a linear 0-1M sodium chloride gradient in starting buffer. The fractions containing rTGF-β2 were pooled and applied to a C4 Vydac column (4.6×250 mm) previously equilibrated with 0.5% trifluoroacetic acid (TFA) in water. rTGF-β2 was eluted using a linear 25%-35% gradient of acetonitrile containing 0.05% TFA.

For amino acid sequence analysis, rTGF-β2 was reduced with 20 mM dithiothreitol in 100 μl of 0.4M Tris-HCl buffer, pH 8.5, containing 6M guanidine/HCl and 0.1% Na$_2$ EDTA, for 2 hours at 50° C., and subsequently S-pyridylethylated with 100 mM 4-vinylpyridine for 18 hours at 23° C. The reaction mixture was acidified with 20% TFA to pH 2.0 and desalted by reversed-phase HPLC (Marquardt et al., 1987, J. Biol. Chem. 262:12127-12131). For cleavage at methionyl residues, 60 pM of S-pyridylethylated rTGF-β2 was treated with CNBr in 70% formic acid. Automated sequence analysis was performed on a model 475A amino acid sequencer (Applied Biosystems, Inc., Foster City, Calif.), as described (Marquardt et al., 1987, J. Biol. Chem. 262:12127-12131).

10.2. RESULTS

10.2.1. Recombinant TGF-β2 is Secreted in a Latent Form

CHO cells were transfected with pTGF-β2(414) and amplified with methotrexate as described in Section 10.1.3., supra. Two clones, β1(414)c1.32 and β2(414)c1.35, isolated by cloning to limiting dilution in 96 well plates, were chosen for further characterization. FIG. 11A and FIG. 11B show that β2(414)c1.32 secretes approximately 5 μg/ml rTGF-β2 and that acid activation is required for detection of maximal bioactivity. Similar results are obtained for β2(414)c1.35. Northern blot analysis shows that β2(414)c1.32 cells contain a major 1.9 kb TGF-β2-specific RNA species which is not detected in normal CHO cells (FIG. 11C).

10.2.2. Analysis of Recombinant TGF-β2 Proteins Secreted by Transfected CHO Cells FIG. 12A shows the regions of TGF-β2-414 precursor against which anti-peptide antibodies were raised. Anti-TGF-β2(414)$_{367-379}$ is specific for TGF-β2, does not react with TGF-β1, and all immunoreactivity can be blocked by excess peptide. Similar specificities were obtained with anti-TGF-β2(414)$_{51-66}$.

FIG. 12B shows the results of immunoblotting of the TGF-β2-related proteins secreted by β2(414)c1.32 cells; for ease of comparison, they are shown alongside the TGF-β1 specific proteins secreted by β1c1.17 cells. β1c1.17 cells secrete a 44-56 kD species (band 'a', FIG. 12B, lane 1) consisting of pro-TGF-β1, and a 30-42 kD species (band 'b', FIG. 12B, lane 1) consisting of the pro-region of TGF-β1 when proteins are separated by SDS-PAGE under reducing conditions and analyzed by immunoblotting with anti-TGF-β1$_{81-94}$. β2(414)c1.32 cells also secrete proteins in this molecular weight range which are detected by anti-TGF-β2(414)$_{51-66}$ (FIG. 12B, lane 2). Note that β2(414)c1.32 cells secrete less of the uncleaved pro-TGF-β2 (band 'a') relative to the cleaved pro-region of the TGF-β2 precursor (band 'b') that do β1c1.17 cells. When immunoblotting is performed with an anti-peptide antibody directed against the mature region of the TGF-β1 precursor (anti-TGF-β1$_{369-381}$), the 44-56 kD pro-TGF-β1 species (band 'a', FIG. 12B, lane 3) as well as the 12 kD TGF-β1 monomer (band 'c', FIG. 12B, lane 3) are detected in supernatants conditioned by β1c1.17 cells. Anti-TGF-β2(414)$_{367-379}$ also detected a 45-56 kD species (band 'a', FIG. 12B, lane 4) and the 12 kD TGF-β2 monomer (band 'c', FIG. 12B, lane 4) in supernatants conditioned by β2(414)c1.32 cells suggesting that band 'a' contains both mature and pro-region TGF-β2-specific sequences, while band 'b' contains only pro-region sequences (see FIG. 12A). Note the decreased amount of band 'a' relative to band 'c' in β2(414)c1.32 cell supernatants compared to supernatants conditioned by β1c1.17 cells.

When media conditioned by β1c1.17 cells was fractionated by SDS-PAGE under non-reducing conditions and analyzed by immunoblotting using anti-TGF-β1$_{81-94}$, a major 90-110 kD species was detected (FIG. 12C, lane 1). When the same analysis is performed with β2(414)c1.32 conditioned media using anti-TGF-β2(414)$_{51-66}$, the 90-110 kD species as well as the mature 24 kD TGF-β1dimer can be seen (FIG. 12C, lane 3). Anti-TGF-$\beta$2(414)$_{367-379}$ detects bands I and II as well as the mature TGF-$\beta$2 (arrow in FIG. 12C) in supernatants conditioned by $\beta$2(414)c1.32 cells (FIG. 12C, lane 4). Since band III was not detected by this antiserum, this species evidently lacks mature TGF-$\beta$2 sequences and consists of pro-region dimers only.

FIG. 12D and FIG. 12E show an analysis of total protein secreted by $\beta$1c1.17, $\beta$2(414)c1.32 and $\beta$2(414)c1.35 after [$^{35}$S]-cysteine and [$^{35}$S]-methionine labeled conditioned media was fractionated by SDS-PAGE under non-reducing (FIG. 12D) and reducing (FIG. 12E) conditions. Note the increased amount of mature TGF-$\beta$2 (arrow, FIG. 12D) and the decrease in the amount of band 'a' relative to band 'c' (FIG. 12E) in supernatants conditioned by $\beta$2(414)c1.32 and $\beta$2(414)c1.35 compared to supernatants conditioned by $\beta$1c1.17. Note, also, that the TGF-$\beta$2-related proteins represent a major portion of the total proteins secreted by $\beta$2(414)c1.32 and $\beta$2(414)c1.35 cells.

10.2.3. Glycosylation and Phosphorylation of Pro-region rTGF-$\beta$2 Precursor Recombinant TGF-$\beta$1 precursor is glycosylated at three sites within the pro-region and contains mannose-6-phosphate (M-6-P) at two of these three sites (Brunner et al., 1988, Mol. Cell. Biol. 8:2229-2232; Purchio et al., 1988, J. Biol. Chem. 263:14211-14215). To determine if the same modifications occur in the TGF-$\beta$2-414 precursor, $\beta$2(414)c1.32 cells were labeled with [$^3$H]-glucosamine and [$^{32}$P]-orthophosphate and serum- and cell-free conditioned media were analyzed by SDS-PAGE. FIGS. 13A and 13B show pro-region of the TGF-$\beta$2 precursor is phosphorylated (FIG. 13A, lane 2) and glycosylated (FIG. 13B, lane 4). The high molecular weight material seen in lane 4 of FIG. 13B does not appear to be related to TGF-$\beta$2precursor as judged by immunoblotting (FIGS. 12A-12E), and is not seen in media conditioned by [$^3$H]-glucosamine labeled $\beta$2(414)c1.35 cells (FIG. 13B, lane 5); it most likely is a non-specific product secreted by this particular clone. As is the case for TGF-$\beta$1, no [$^{32}$P] or [$^3$H]-glucosamine label is found in the TGF-$\beta$2 12 kDa monomer.

FIG. 14A shows the results of two-dimensional electrophoretic analysis of acid hydrolysates of [$^{32}$P]-labeled rTGF-$\beta$1 precursor, and indicates the position of migration of the M-6-P residue contained within this molecule. Similar analysis performed with [$^{32}$P]-labeled pro-TGF-$\beta$2-414 secreted by $\beta$2(414)c1.32 cells shows that the label does not co-mitrate with P-Ser, P-Thr or P-Tyr (FIG. 14B), but does not co-migrate with M-6-P (FIG. 14C).

10.2.4. Purification and Sequence Analysis of Mature Recombinant TGF-$\beta$2

Mature rTGF-$\beta$2 was purified from $\beta$2(414)c1.32-conditioned serum-free media as described in Section 10.1.8., supra. FIG. 15 shows that the purified protein migrates as a 12 kD species under reducing conditions (FIG. 15, lane 1); under non-reducing conditions it migrates with a molecular weight of 24 kD (FIG. 15, lane 2), identical to purified rTGF-$\beta$1 (FIG. 15, lane 3). rTGF-$\beta$2 was further characterized by protein sequence analysis (Table 2, below). S-pyridylethylated rTGF-$\beta$2 was cleaved with cyanogen bromide at residue 104 and the two peptides obtained were sequenced simultaneously: one corresponded to the amino-terminal sequence and the other corresponded to the carboxy-terminal sequence 105-112. The results demonstrate that biologically active rTGF-$\beta$2 is correctly processed at the predicted cleavage sites.

TABLE 2

AMINO ACID SEQUENCE DATA FOR rTGF-$\beta$2 HPLC-purified rTGF-$\beta$2

| Amino-terminal | | Carboxy-terminal | |
| --- | --- | --- | --- |
| Yield (pmol) | Position (residue) | Yield (pmol) | Position (residue) |
| 56.1 | 1 (Ala) | 58.7 | 105 (Ile) |
| 82.3 | 2 (Leu) | 77.7 | 106 (Val) |
| 55.8 | 3 (Asp) | 62.1 | 107 (Lys) |
| 70.2 | 4 (Ala) | 34.7 | 108 (Ser) |
| 79.3 | 5 (Ala) | 53.0 | 109 (Cys) |
| 51.5 | 6 (Tyr) | 39.8 | 110 (Lys) |
| 38.0 | 7 (Cys)[1] | 38.0 | 111 (Cys)[1] |
| 43.4 | 8 (Phe) | 14.8 | 112 (Ser) |

[1]S-pyridylethylated rTGF-$\beta$2 was cleaved with CNBr. Two sequences, rTGF-$\beta$2 (1-104) and rTGF-$\beta$2 (105-112), were obtained in nearly equimolar yields as determined from the yields in cycles 1 (56.1 pmol PTH Ala-1 and 58.7 pmol Ile-105) and 7 (76.0 pmol PTH Cys-7 and PTH Cys-111).

11. DEPOSIT OF MICROORGANISMS

The following microorganisms have been deposited with the Agricultural Research Culture Collection, Northern Regional Research Center (NRRL) and have been assigned the following accession numbers;

| Microorganism | Plasmid | Accession No. |
| --- | --- | --- |
| *Escherichia coli* HB101 | pPC-21 | B-18256 |
| *Escherichia coli* HB101 | pPC-14 | B-18333 |
| *Escherichia coli* HB101 | pBSC-40-1 | B-18335 |
| *Escherichia coli* HB101 | pBSC-40-16 | B-18334 |

The following transfectants have been deposited with the American Type Culture Collection, Rockville, Md., and have been assigned the listed accession numbers:

| Transfectants | Plasmid | Accession No. |
| --- | --- | --- |
| Chinese Hamster Ovary (CHO) 1$\beta$9, 12.5 CL 36 | pSV2/$\beta$1-$\beta$/dhfr | CRL 9800 |
| Chinese Hamster Ovary (CHO) $\beta$2(414)c1.32 | pTGF-$\beta$2(414) | 10300 |

The present invention is not to be limited in scope by the cell lines deposited or the embodiments disclosed herein which are intended as single illustrations of one aspect of the invention and any which are functionally equivalent are within the scope of the invention. Indeed, various modifications of the invention, in addition to those shown and described herein, will become apparent to those skilled in the art from the foregoing description. Such modifications are intended to fall within the scope of the appended claims.

It is also to be understood that all base pair and amino acid residue numbers and sizes given for nucleotides and peptides are approximate and used for the purposes of description.

What is claimed is:

1. An isolated and purified nucleotide sequence encoding a hybrid transforming growth factor-$\beta$1/transforming growth factor-$\beta$2 precursor, said nucleotide sequence comprising a simian TGF-$\beta$1 precursor coding sequence upstream from and joined in frame with a human TGF-$\beta$2 mature coding sequence, as depicted in FIGS. 1D through 1F from about nucleotide residue number $-70$ to about nucleotide residue number 1755.

2. The cell line CHO 1$\beta$9, 12.5, CL 36 as deposited with the ATCC and assigned accession number CRL 9800.

* * * * *